United States Patent
Saito et al.

(10) Patent No.: US 10,689,624 B2
(45) Date of Patent: Jun. 23, 2020

(54) COMPOUND FOR IDENTIFYING PLURIPOTENT CELLS

(71) Applicant: KYOTO UNIVERSITY, Kyoto-shi, Kyoto (JP)

(72) Inventors: Hirohide Saito, Kyoto (JP); Yi Kuang, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 15/543,488

(22) PCT Filed: Jan. 14, 2016

(86) PCT No.: PCT/JP2016/050946
§ 371 (c)(1),
(2) Date: Jul. 13, 2017

(87) PCT Pub. No.: WO2016/114341
PCT Pub. Date: Jul. 21, 2016

(65) Prior Publication Data
US 2018/0002673 A1 Jan. 4, 2018

(30) Foreign Application Priority Data
Jan. 14, 2015 (JP) .................. 2015-005107

(51) Int. Cl.
| | | |
|---|---|---|
| *C12N 5/00* | (2006.01) | |
| *C12N 5/16* | (2006.01) | |
| *C12N 5/10* | (2006.01) | |
| *C07C 229/36* | (2006.01) | |
| *C07K 14/00* | (2006.01) | |
| *C08G 69/10* | (2006.01) | |
| *G01N 33/50* | (2006.01) | |

(52) U.S. Cl.
CPC .............. *C12N 5/16* (2013.01); *C07C 229/36* (2013.01); *C07K 14/001* (2013.01); *C08G 69/10* (2013.01); *C12N 5/10* (2013.01); *G01N 33/5073* (2013.01)

(58) Field of Classification Search
CPC .................. C12N 5/16; C12N 5/0695
See application file for complete search history.

(56) References Cited

FOREIGN PATENT DOCUMENTS

| | | |
|---|---|---|
| JP | 2013-000974 A | 1/2013 |
| JP | 2013-9742 A | 1/2013 |
| WO | WO 2013/186946 | 12/2013 |
| WO | 2015/157535 A2 | 10/2015 |

OTHER PUBLICATIONS

Liang et al. Chem. Commun. 1096-4098, 2007 (Year: 2007).*
Li et al. "Supramolecular Nanofibers and Hydrogels of Nucleopeptides", *Angew. Chem. Int. Ed.* 50:9365-9369 (2011).
Muramatsu et al. "Carbohydrate markers of ES cells"), *Trends in Glycoscience and Glycotechnology* 21(120):197-206 (2009).
International Search Report corresponding to International Application No. PCT/JP2016/050946, dated Apr. 12, 2016.
Matsuda et al. "Emerging Innovation towards safety in the clinical application of ESCs and IPSCs", Nature Reviews Cardiology published online Aug. 5, 2017: doi:10.1038/nrcardio.2014.9-c1.
Shi et al. "D-Amino Acids Modulate the Cellular Response of Enzymatic-Instructed Supramolecular Nanofibers of Small Peptides", Biomacromolecules 15:3559-3568 (2014).
Tohyama et al. "Distinct Metabolic Flow Enables Large-Scale Purification of Mouse and Human Pluripotent Stem Cell-Derived Cardiomyocytes", Cell Stem Cell 12:127-137 (2013).
Wang et al. "A structure-gelation ability study in a short peptide-based Super Hydrogelator system", Soft Matter 7:3897-3905 (2011).
Extended European Search Report corresponding to European Application No. 16737412.3 dated Jul. 2, 2018.
Shevinsky et al. "Monoclonal Antibody to Murine Embryos Defines a Stage-Specific Embryonic Antigen Expressed on Mouse Embryos and Human Teratocarcinoma Cells", Cell 30;697-705 (1982).
Takahashi et al. Induction of Pluripotent Stem Cells from Adult Human Fibroblasts by Defined Factors, *Cell* 131:861-872 (2007).
Thomson et al. "Embryonic Stem Cell Lines Derived from Human Blastocysts", *Science* 282:1145-1147 (1998).
Kuang et al. "Pericellular Hydrogel/Nanonets Inhibit Cancer Cells", Angew. Chem. Int. Ed. 53:8104-8107 (2014).
Li et al. "An enzyme-assisted nanoparticle crosslinking approach to enhance the mechanical strength of peptide-based supramolecular hydrogels", Chem. Commun. 49:8653-8655 (2013).
Office Action corresponding to Japanese Application No. 2016-569500 dated Jan. 23, 2020.

* cited by examiner

*Primary Examiner* — Marcia S Noble
(74) *Attorney, Agent, or Firm* — Myers Bigel, P.A.

(57) ABSTRACT

[Problem to be Solved]
To provide a compound for removing pluripotent cells from a cell population potentially containing the pluripotent cells.
[Solution]
A polyphenylalanine derivative is contacted with a cell population of interest.

5 Claims, 14 Drawing Sheets in Stemfit in DMEM

COMPOUND FOR IDENTIFYING PLURIPOTENT CELLS

RELATED APPLICATIONS

This application is a 35 U.S.C. § 371 national phase application of PCT Application PCT/JP2016/050946 filed Jan. 14, 2016, which claims priority to Japanese Application No. 2015-005107 filed Jan. 14, 2015. The entire contents of each are incorporated herein by reference in its entirety.

FIELD OF THE INVENTION

The present invention relates to a compound used for selectively removing pluripotent cells from a cell specimen containing the pluripotent stem cells and cells differentiated from the pluripotent stem cells.

BACKGROUND OF THE INVENTION

Pluripotent stem cells, such as human embryonic stem (ES) cells (Non Patent Literature 1) and induced pluripotent stem (iPS) cells (Non Patent Literature 2), are cells proliferating infinitely and differentiating into various cell types, and thus are expected as a material for regenerative medicine. However, since the transplantation of a cell specimen containing a small amount of undifferentiated cells resulted in teratomas in an animal model, concern over its safety has been raised. Thus, it is necessary to remove such undifferentiated cells, that is, cells that are pluripotent.

To detect such human pluripotent stem cells, an antibody to SSEA-4 (stage-specific embryonic antigen 4) has been widely used (Non Patent Literature 3). To remove pluripotent cells from a cell population using SSEA-4 as an index, it is necessary to perform sorting with a flow cytometer or the like using the antibody to SSEA-4. At this time, since the antibody is used, there is concern that the transplantation material is contaminated with the antibody; thus, there is need for a method for selectively removing pluripotent cells by another method.

CITATION LIST

Non Patent Literature

Non Patent Literature 1: Thomson, J. A. et al. Science 1998, 282, 1145-1147
Non Patent Literature 2: Takahashi, K. et al. Cell 2007, 131, 861-872
Non Patent Literature 3: Shevinsky, L. H. et al. Cell 1982, 30, 697-705

SUMMARY OF INVENTION

As a result of intensive studies on a compound selectively leading pluripotent cells to cell death, the present inventors have discovered that a polyphenylalanine derivative can selectively induce the cell death of only pluripotent stem cells, thereby accomplishing the present invention.

The present invention has the following features.

[1] A method for removing pluripotent cells, comprising a step of contacting a compound represented by formula (I):

[Formula 1]

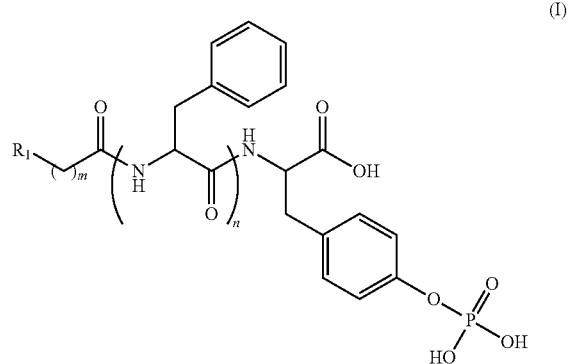

(I)

wherein $R_1$ represents an aryl group or a heteroaryl group; m represents an integer of 1 to 6; and n represents an integer of 2 or more, or formula (II):

[Formula 2]

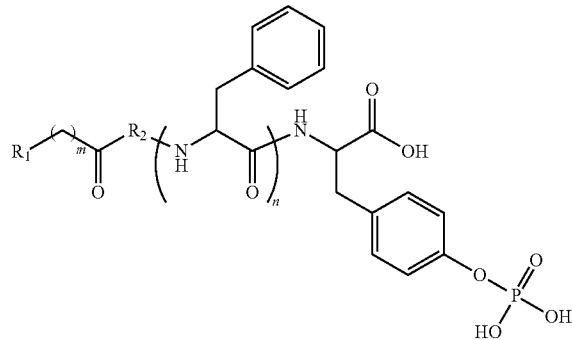

(II)

wherein $R_1$ represents an aryl group or a heteroaryl group; $R_2$ represents an alanine residue or a glycine residue; m represents an integer of 1 to 6; and, n represents an integer of 2 or more, with a cell population of interest.

[2] The method according to [1], wherein the compound is a compound represented by the formula (I), wherein $R_1$ represents a naphthyl group and m represents 1.

[3] The method according to [2], wherein the compound is a compound represented by the formula (I), wherein n represents 3.

[4] The method according to any one of [1] to [3], wherein the cell population of interest is a cell population differentiation-induced from pluripotent stem cells.

[5] A kit for removing pluripotent cells, comprising a compound represented by formula

[Formula 3]

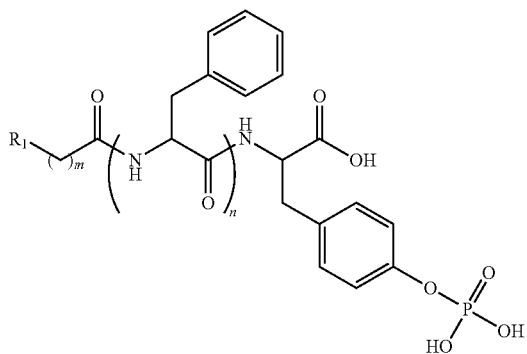

wherein $R_1$ represents an aryl group or a heteroaryl group; n represents an integer of 1 to 6; and represents an integer of 2 or more, or formula (II):

[Formula 4]

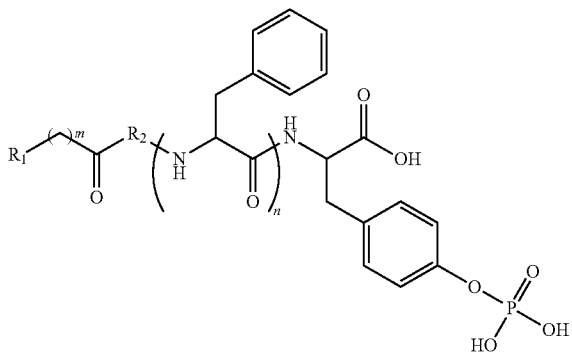

wherein $R_1$ represents an aryl group or a heteroaryl group; $R_2$ represents an alanine residue or a glycine residue; m represents an integer of 1 to 6; and n represents an integer of 2 or more.

[6] The kit according to [5], wherein the compound is a compound represented by the formula (I), wherein $R_1$ represents a naphthyl group and m represents 1.

[7] The kit according to [6], wherein the compound is a compound represented by the formula (I), wherein n represents 3.

Advantageous Effects of Invention

According to the present invention, the polyphenylalanine derivative can be applied to removing, from a cell group of interest, contained pluripotent cells since it has an action of leading the pluripotent cells to cell death.

DESCRIPTION OF EMBODIMENTS

Figure 1:
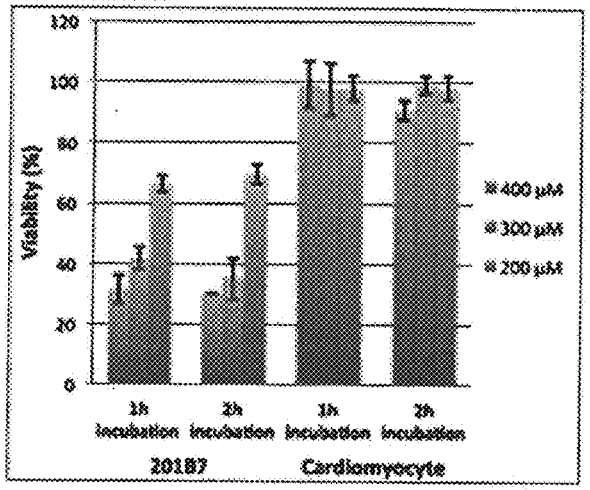
FIG. 1 is a series of graphs showing the viability of 201B7 or a cardiomyocyte cell line cultured in Stemfit (upper left) and StemPro (upper right) for 1 day after contacting the respective cells with D-3 for 1 hour (1 h) or 2 hours (2 h), and the viability of NHDF (normal human dermal fibroblasts) (lower left) or HS-5 (normal human marrow stroma cells) (lower right) as normal cell lines cultured in DMEM for 1 day after contacting the respective cells with D-3 for 1 hour (1 h) or 2 hours (2 h). The ordinate represents, as cell viability, values calculated by setting each of the results of performing the same experiments without contacting with D-3 to 100%.
Figure 1:
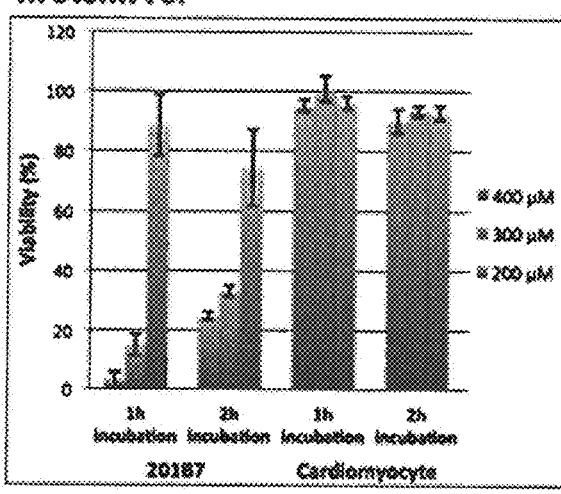
Figure 1:
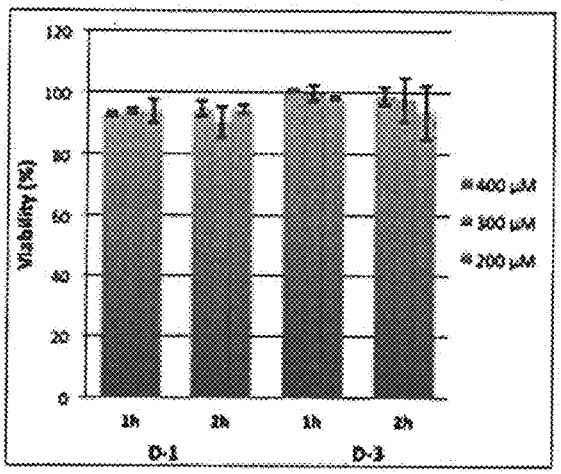
Figure 1:
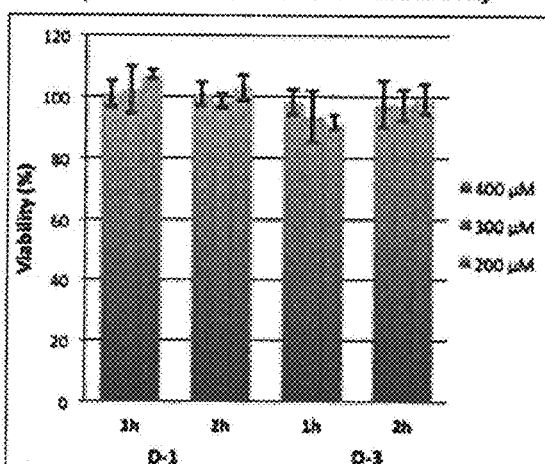

The present invention provides a method for removing pluripotent cells, comprising a step of contacting a polyphenylalanine derivative represented by formula (I):

[Formula 5]

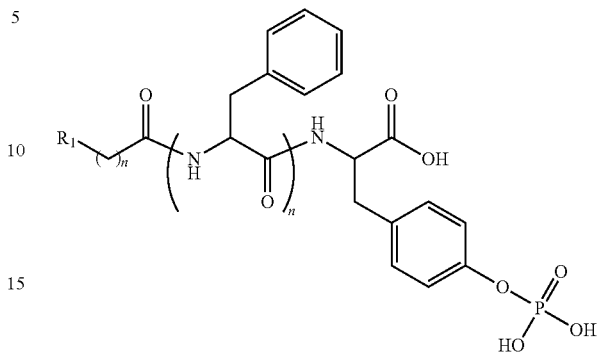

(I)

wherein $R_1$ represents an aryl group or a heteroaryl group m represents an integer of 1 to 6; and n represents an integer of 2 or more, or formula (II):

[Formula 6]

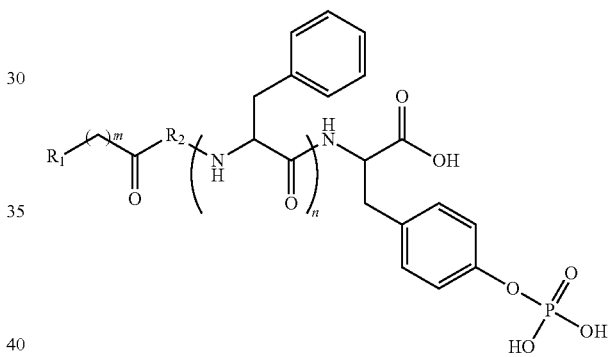

(II)

wherein $R_1$ represents an aryl group or a heteroaryl group; $R_2$ represents an alanine residue or a glycine residue; in represents an integer of 1 to 6; and n represents an integer of 2 or more, with a cell population of interest, or a kit for removing pluripotent cells, comprising the polyphenylalanine derivative.

For the purpose of the present invention, the aryl group refers to a monovalent 6-carbon monocyclic, 10-carbon bicyclic, or 14-carbon tricyclic aromatic ring system. Examples of the aryl group include, but not limited to, a phenyl group, a naphthyl group, and an anthracenyl group.

For the purpose of the present invention, the heteroaryl group refers to a monovalent aromatic 5- to 8-membered monocyclic, 8- to 12-membered bicyclic, or 11- to 14-membered tricyclic system having 1 or more hetero atoms (e.g., O, N, S, or Se). Examples of the heteroaryl group include a pyridyl group, a furyl group, an imidazolyl group, a benzimidazolyl group, a pyrimidinyl group, a thienyl group, a quinolinyl group, an indolyl group, and a thiazolyl group.

Unless otherwise stated, as used herein, the aryl group includes both substituted and unsubstituted moieties. The term "substituted" refers to having 1 or more substituents (which may be the same or different), each of which substitutes a hydrogen atom. Examples of the substituent include, but not limited to, halogen groups (e.g., F, Cl, Br, and I), a hydroxyl group, an amino group, a cyano group, a nitro group, a mercapto group, an alkoxycarbonyl group, an acyloxy group, an amide group, a carboxy group, an alkanesulfonyl group, an alkylcarbonyl group, a carbamide group, a carbamyl group, a carboxyl group, a thioureido group, a thiocyanate group, a sulfonamido group, an alkyl group, an alkenyl group, an alkynyl group, an alkyloxy group, an aryl group, a heteroaryl group, a cycloalkyl group, and a heterocyclylalkyl group; among these, the alkyl group, the alkenyl group, the alkynyl group, the alkyloxy group, the aryl group, the heteroaryl group, the heteroaryloxy group, the alkylamino group, the arylamino group, the oxo group (O═), the thioxo group (S═), the thio group, the silyl group, the alkylthio group, the arylthio group, the alkylsulfonyl group, the arylsulfonyl group, the acylamino group, the aminoacyl group, the aminothioacyl group, the amidino group, the thioureido group, the thiocyanate group, the sulfonamido group, the guanidine group, the ureido group, the acyl group, the thioacyl group, the carbamyl group (—C(O)NH$_2$), the carboxyl group (—COOH), and the carboxylic acid ester, especially, the alkyl group, the alkenyl group, the alkynyl group, the alkyloxycarbonyl group, the aryl group, the heteroaryl group, the cyclyl group, and the heterocyclyl group, can be further substituted. The cycloalkyl group, the cycloalkenyl group, the heterocycloalkyl group, the heterocycloalkenyl group, the aryl group, and the heteroaryl group can be annelated to each other. The substituent may be a protecting group in the process of synthesis. The "protecting group" herein refers to a group or moiety used for protecting or blocking a functionality undergoing an undesired reaction during process steps.

The protecting group prevents the reaction during the steps; however, it can thereafter be removed to exhibit its primary functionality. Examples of the protecting group include, but not limited to, a trimethylsilyl group (TES), a tert-butyloxycarbonyl group (tBoc), a benzyloxycarbonyl group (CBZ), and a 9-fluorenylmethyloxycarbonyl group (Fmoc).

According to the present invention, the polyphenylalanine derivative is preferably a compound represented by formula

[Formula 7]

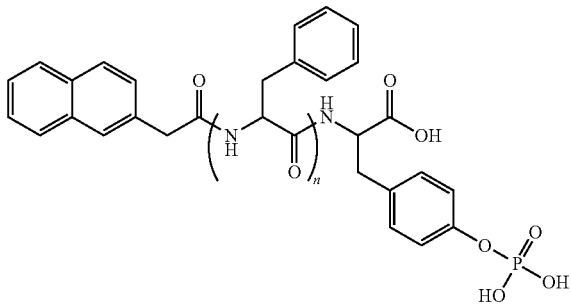

(III)

in which in the formula (I), R$_1$ is a naphthyl group and m is 1.

According to the present invention, the polyphenylalanine derivative is more preferably a compound of formula (III), wherein n is 3.

The alanine residue, the glycine residue, the phenylalanine residue, and the O-phospho-D-tyrosine contained in the polyphenylalanine derivative of the present invention may be in D-form or L-form, and is preferably in D-form in view of being less easily decomposed.

The polyphenylalanine derivative of the present invention can be synthesized properly using amino acids or carboxylic acids by a solid phase peptide synthesis method known per se.

For the purpose of the present invention, the pluripotent cell is a cell which has the property of being capable of differentiating into all cells present in a living body and is positive for at least one marker gene selected from the group consisting of alkaline phosphatase, Oct-3/4, Nanog, SSEA-3, SSEA-4, TRA-1-60, and TRA-1-81. The pluripotent cell includes a pluripotent stem cell.

According to the present invention, the cell population of interest is not particularly limited provided that it is a cell population at risk of containing pluripotent cells; however, examples thereof include a cell population differentiation-induced from pluripotent stem cells.

According to the present invention, the pluripotent stem cell has pluripotency enabling differentiation into all cells present in a living body and also has proliferative capacity. Examples of the pluripotent stem cell include, but are not limited to, an embryonic stem (ES) cell, a cloned embryo-derived embryonic stem cell obtained by nuclear transplantation ("ntES cell"), a germ stem cell ("GS cell"), an embryonic germ cell ("EG cell"), and an induced pluripotent stem (iPS) cell. Preferred examples of the pluripotent stem cell include an ES cell, an ntES cell, and an iPS cell.

(A) Embryonic Stem Cell

The ES cell is a stem cell having pluripotency and proliferative capacity by self-replication, established from the inner cell mass of an early embryo (e.g., a blastocyst) of a mammal, such as a human or a mouse.

The ES cell is an embryo-derived stem cell derived from the inner cell mass of a blastocyst as an embryo at the 8-cell stage of fertilized egg and after the morula stage, and has the ability to differentiate into all cells constituting an adult, so-called pluripotent differentiation ability, and proliferative capacity by self-replication. The ES cell was discovered in mice in 1981 (M. J. Evans and M. H. Kaufman (1981), Nature 292: 154-156), and then ES cell lines were also established in primates, such as a human and a monkey (J. A. Thomson et al. (1998), Science 282: 1145-1147; J. A. Thomson et al. (1995), Proc. Natl. Acad. Sci. USA, 92:7844-7848; J. A. Thomson et al. (1996), Biol. Reprod., 55:254-259; and J. A. Thomson and V. S. Marshall (1998), Curr. Top. Dev. Biol., 38: 133-165).

The ES cell can be established by taking out the inner cell mass from the blastocyst of fertilized egg of an animal of interest and culturing the inner cell mass on fibroblasts as feeder cells. The maintenance of cells by subculture can be carried out using a medium containing substances, such as leukemia inhibitory factor (LIF) and basic fibroblast growth factor (bFGF). Methods for establishing and maintaining human and monkey ES cells are described, for example, in H. Suemori et al. (2006), Biochem. Biophys. Res. Commun., 345: 926-932; M. Ueno et al. (2006), Proc. Natl. Acad. Sci. USA, 103: 9554-9559; H. Suemori et al. (2001), Dev. Dyn., 222: 273-279; and H. Kawasaki et al. (2002), Proc. Natl. Acad. Sci. USA, 99: 1580-1585.

The human ES cell can be maintained, for example, in a wet atmosphere at 37° C. and 5% CO2 using DMEM/F-12 medium supplemented with 0.1 mM 2-mercaptoethanol, 0.1 mM non-essential amino acid, 2 mM L-glutamic acid, 20% KSR, and 4 ng/ml bFGF. The ES cell should be passaged every 3 to 4 days, and at this time, the passage can be carried out, for example, using 0.25% trypsin and 0.1 mg/ml collagenase IV in PBS containing 1 mM CaCl2 and 20% KSR.

The ES cell can be typically selected using the expression of gene markers, such as alkaline phosphatase, Oct-3/4, and Nanog, as indexes. Particularly, the human ES cell can be selected by detecting the expression of gene markers, such as Oct-3/4, and Nanog, by a real-time PCR method or detecting SSEA-3, SSEA-4, TRA-1-60, and TRA-1-81 as cell surface antigens by an immunostaining method (Klimanskaya I, et al. (2006), Nature. 444: 481-485).

Human ES cell lines, for example, KhES-1, KhES-2, and KhES-3, are available from the Institute for Frontier Medical Sciences, Kyoto University (Kyoto, Japan).

(B) Germ Stem Cell

The germ stem cell is a testis-derived pluripotent stem cell and a cell providing a source for spermatogenesis. This cell can be differentiation-induced into cells of various lineages like an ES cell, and has, for example, the property of being capable of producing a chimeric mouse when transplanted into a mouse blastocyst (M. Kanatsu-Shinohara et al. (2003) Biol. Reprod., 69: 612-616; K. Shinohara et al. (2004), Cell, 119: 1001-1012). The germ stem cell can self-replicate in a medium containing a glial cell line-derived neurotrophic factor (GDNF), and passage can be repeated under culture conditions similar to those for an ES cell to provide the germ stem cell (Masanori Takebayashi et al. (2008), Experimental Medicine, vol. 26, No. 5 (extra issue), p. 41-46, Yodosha Co., Ltd. (Tokyo, Japan)).

(C) Embryonic Germ Cell

The embryonic germ cell is a cell having pluripotency similar to that of an ES cell, established from a primordial germ cell during the prenatal period, and can be established by culturing the primordial germ cell in the presence of substances, such as LIF, bFGF, and a stem-cell factor (Y. Matsui et al. (1992), Cell, 70: 841-847; J. L. Resnick et al. (1992), Nature, 359:550-551).

(D) Induced Pluripotent Stem Cell

The induced pluripotent stem (iPS) cell is a somatic cell-derived artificial stem cell having almost the same characteristics, such as pluripotent differentiation ability and proliferative capacity by self-replication, as those of an ES cell, which can be prepared by introducing a particular nuclear reprogramming substance into a somatic cell in the form of DNA or protein or increasing the expression of endogenous mRNA and protein of the nuclear reprogramming substance using an agent (K. Takahashi and S. Yamanaka (2006) Cell, 126: 663-676; K. Takahashi et al. (2007) Cell, 131: 861-872; J. Yu et al. (2007) Science, 318: 1917-1920; M. Nakagawa et al. (2008) Nat. Biotechnol., 26: 101-106; International Publication No. WO2007/069666; and International Publication No. WO2010/068955). The nuclear reprogramming substance is not particularly limited provided that it is a gene specifically expressed in an ES cell or a gene playing an important role in maintaining the undifferentiation of an ES cell, or a gene product thereof; however, examples thereof include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmil, Lin28, Lin28b, Nanog, Esrrb, Esrrg, and Glis1. These nuclear reprogramming substances may be used in combination in establishing an iPS cell. For example, the nuclear reprogramming substances are used in combination including at least 1, or 2 or 3, preferably 4, thereof.

The information of the nucleotide sequences of mouse and human cDNAs of each of the nuclear reprogramming substances and the amino acid sequences of proteins encoded by the cDNAs can be obtained by referring to the NCBI accession numbers described in International Publication No. WO2007/069666. The information of the mouse and human cDNA sequences and amino acid sequences of L-Myc, Lin28, Lin28b, Esrrb, Esrrg, and Glis1 can be obtained by referring to the following NCBI accession numbers. One skilled in the art can prepare desired nuclear reprogramming substances by conventional methods, based on the information of the cDNA sequences or amino acid sequences.

| Gene Name | Mouse | Human |
| --- | --- | --- |
| L-Myc | NM_008506 | NM_001033081 |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| Glis1 | NM_147221 | NM_147193 |

These nuclear reprogramming substances may be each introduced in the form of a protein into a somatic cell by a technique, such as lipofection, binding to a cell membrane-permeable peptide or microinjection, or may be introduced in the form of DNA into a somatic cell by a technique, such as using a vector (e.g., virus, plasmid, or artificial chromosome vector), lipofection, liposome, or microinjection. Examples of the virus vector include retroviral vectors, lentivirus vectors (both are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated viral vectors, and Sendai virus vectors (Proc. Jpn. Acad. Ser. B. Phys. Biol. Sci. 85, 348-62, 2009). Examples of the artificial chromosome vector include a human artificial chromosome (HAC), a yeast artificial chromosome (YAC), and bacterial artificial chromosomes (BAC, PAC). As the plasmid, a plasmid for mammalian cells can be used (Science, 322: 949-953, 2008). The vector can contain control sequences, such as a promoter, an enhancer, a ribosomal binding sequence, a terminator, and a polyadenylation site. Examples of the used promoter include EF1α promoter, CAG promoter, SRα promoter, SV40 promoter, LRT promoter, CMV (cytomegalovirus) promoter, RSV (Rous sarcoma virus) promoter, MoMuLV (Moloney murine leukemia virus) LTR, and HSV-TK (herpes simplex virus thymidine kinase) promoter. Among others, EF1α promoter, CAG promoter, MoMuLV LTR, CMV promoter, and SRα promoter are preferable. In addition, the vector may contain a selection marker sequence, such as a drug resistance gene (e.g., a kanamycin-resistant gene, an ampicillin-resistant gene, or a puromycin-resistant gene), a thymidine kinase gene, or a diphtheria toxin gene; a reporter gene sequence, such as a green fluorescence protein (GFP), β-glucuronidase (GUS), or FLAG; and the like, if necessary. In order to remove a gene encoding a nuclear reprogramming substance or both of a promoter and the gene encoding a nuclear reprogramming substance binding thereto after introduction into a somatic cell, the vector may also have LoxP sequences thereacross. In another preferable embodiment, after incorporating a transgene in a chromosome by using a transposon, a method can be used which involves completely removing the transgene from the chromosome by causing a transferase to act on the cell using a plasmid vector or an adenovirus vector. Preferred examples of the transposon include piggyBac as a transposon derived from a lepidopteran insect (Kaji, K. et al., (2009), Nature, 458: 771-775, Woltjen et al., (2009), Nature, 458: 766-770, and International Publication No. WO2010/012077). Further, the vector may contain the origin of lymphotrophic herpes virus, BK virus, or Bovine papillomavirus and a sequence responsible for the replication thereof so that it is replicated in the absence of incorporation into a chromosome and episomally present. Examples thereof include containing EBNA-1 and oriP sequences or Large T and SV40ori sequences (International Publication Nos. WO2009/115295, WO2009/157201, and WO2009/149233). An expression vector for polycistronic expression may be used to simultaneously introduce a plurality of nuclear reprogramming substances. For polycistronic expression, gene-encoding sequences may be bound to each other through IRES or foot-and-mouth disease virus (FMDV) 2A coding region (Science, 322: 949-953, 2008; and International Publication Nos. WO2009/092042 and WO2009/152529).

To increase the efficiency of the induction of an iPS cell in nuclear reprogramming, in addition to the above factors can be used, for example, a histone deacetylase (HDAC) inhibitor [e.g., a small molecule inhibitor, such as valproic acid (VPA) (Nat. Biotechnol., 26(7): 795-797 (2008)), trichostatin A, sodium butyrate, MC1293, or M344, a nucleic acid expression inhibitor, such as siRNA or shRNA against HDAC (e.g., HDAC1 siRNA Smartpool (R) (Millipore)) or HuSH 29 mer shRNA Constructs against HDAC1 (OriGene)], a DNA methyltransferase inhibitor (e.g., 5'-azacytidine) (Nat. Biotechnol., 26(7): 795-797 (2008)), a G9a histone methyltransferase inhibitor [e.g., a small molecular inhibitor, such as BIX-01294 (Cell Stem Cell, 2: 525-528 (2008)), or a nucleic acid expression inhibitor, such as siRNA or shRNA against G9a (e.g., G9a siRNA (human) (Santa Cruz Biotechnology)], an L-channel calcium agonist (e.g., Bayk8644) (Cell Stem Cell, 3, 568-574 (2008)), a p53 inhibitor (e.g., siRNA and shRNA against p53) (Cell Stem Cell, 3, 475-479 (2008)), a Wnt signaling activator (e.g., soluble Wnt3a) (Cell Stem Cell, 3, 132-135 (2008)), a growth factor such as LIF or bFGF, an ALK5 inhibitor (e.g., SB431542) (Nat. Methods, 6: 805-8 (2009)), a mitogen-activated protein kinase signaling inhibitor, a glycogen synthase kinase-3 inhibitor (PloS Biology, 6(10), 2237-2247 (2008)), and miRNA, such as miR-291-3p, miR-294, or miR-295 (R. L. Judson et al., Nat. Biotech., 27:459-461 (2009)).

Examples of the agent used for increasing the expression of an endogenous protein of a nuclear reprogramming substance include 6-bromoindirubin-3'-oxime, indirubin-5-nitro-3'-oxime, valproic acid, 2-(3-(6-methylpyridin-2-yl)-1H-pyrazol-4-yl)-1,5-naphthyridine, 1-(4-methylphenyl)-2-(4,5,6,7-tetrahydro-2-imino-3(2-H)-benzothiazolyl)ethane HBr (pifithrin-alpha), prostaglandin J2, and prostaglandin E2 (International Publication No. WO2010/068955).

Culture media for inducing iPS cells include, for example, (1) 10 to 15% FBS-containing DMEM, DMEM/F12, or DME medium (these media may further properly contain LIF, penicillin/streptomycin, puromycin, L-glutamine, nonessential amino acids, β-mercaptoethanol, and the like) and (2) a medium for ES cells, containing bFGF or SCF, for example, a medium for mouse ES cells (e.g., TX-WES medium (Thrombo X) or a medium for primate ES cells (e.g., a medium for primate (human and monkey) ES cells (ReproCell, Kyoto, Japan), mTeSR-1).

As an example of a culture method, for example, somatic cells can be contacted with a nuclear reprogramming substance (DNA or protein) in 10% FBS-containing DMEM or DMEM/F12 medium at 37° C. in the presence of 5% $CO_2$ and cultured for about 4 to 7 days, followed by reseeding the cells on feeder cells (for example, mitomycin C-treated STO cells or SNL cells), culturing the cells in a bFGF-containing medium for primate ES cells from about 10 days after the contact between the somatic cells and the nuclear reprogramming substance, and generating ES cell-like colonies about 30 to about 45 days or more after the contact. To increase the efficiency of the induction of iPS cells, culture may also be performed under conditions of an oxygen concentration as low as 5 to 10%.

Alternatively, as an alternative culture method therefor, somatic cells can be cultured in 10% FBS-containing DMEM medium (which may further properly contain LIF, penicillin/streptomycin, puromycin, L-glutamine, nonessential amino acids, β-mercaptoethanol, and the like) on feeder cells (for example, mitomycin C-treated STO cells or SNL cells), followed by generating ES cell-like colonies about 25 to about 30 days or more after the culture.

During the above culture, the medium is replaced with a fresh medium once daily from at or after the second day of starting the culture. The number of the somatic cells used in nuclear reprogramming is not limited; however, it is in the range of about $5 \times 10^3$ to about $5 \times 10^6$ per 100 $cm^2$ of culture dish.

When a gene containing a drug-resistant gene is used as a marker gene, marker gene-expressing cells can be selected by performing culture in a medium containing the corresponding drug (a selection medium). Marker gene-expressing cells can also be detected by observation under a fluorescence microscope when the marker gene is a fluorescent protein gene, by adding a light-emitting substrate when it is a luciferase gene, or by adding a chromogenic substrate when it is a chromogenic enzyme gene.

As used herein, "somatic cell" may be any cell other than a germ cell, derived from a mammal (for example, a human, a mouse, a monkey, a pig, or a rat); examples thereof include keratinized epithelial cells (e.g., a keratinized epidermal cell), mucosal epithelial cells (e.g., an epithelial cell of the tongue surface), exocrine gland epithelial cells (e.g., a mammary gland cell), hormone-secreting cells (e.g., an adrenomedullary cell), cells for metabolism/storage (e.g., a liver cell), luminal epithelial cells forming the interface (e.g., a type I alveolar cell), luminal epithelial cells of an inner chain tube (e.g., a vascular endothelial cell), ciliated cells having transport capacity (e.g., a tracheal epithelial cell), cells for extracellular matrix secretion (e.g., a fibroblast), constrictive cells (e.g., a smooth muscle cell), cells of the blood and the immune system (e.g., a T-lymphocyte), sense-related cells (e.g., a rod cell), autonomic neurons (e.g., a cholinergic neuron), sustentacular cells of sensory organs and peripheral neurons (e.g., a satellite cell), neurons and glial cells in the central nervous system (e.g., an astroglial cell), pigment cells (e.g., a retinal pigment epithelial cell), and progenitor cells (a tissue progenitor cell) thereof. There is no particular limitation on the degree of cell differentiation, the age of an animal from which cells are collected, and the like; even undifferentiated progenitors (including somatic stem cells) or even finally differentiated mature cells can be similarly used as a source of the somatic cells according to the present invention. Here, examples of undifferentiated progenitor cells include tissue stem cells (somatic stem cells), such as a neural stem cell, a hematopoietic stem cell, a mesenchymal stem cell, and a dental pulp stem cell. According to the present invention, the mammal individual from which somatic cells are collected is not particularly limited; however, it is preferably a human.

(E) Cloned Embryo-Derived ES Cell Obtained by Nuclear Transplantation

An nt ES cell is a cloned embryo-derived ES cell prepared by a nuclear transplantation technique, and has almost the same characteristics as those of a fertilized egg-derived ES cell (T. Wakayama et al. (2001), Science, 292: 740-743; S. Wakayama et al. (2005), Biol. Reprod., 72: 932-936; J. Byrne et al. (2007), Nature, 450: 497-502). Specifically, the ES cell established from the inner cell mass of a blastocyst derived from a cloned embryo obtained by replacing the nucleus of a somatic cell with the nucleus of an unfertilized egg is an nt ES (nuclear transfer ES) cell. For the preparation of an nt ES cell, a combination of a nuclear transplantation technique (J. B. Cibelli et al. (1998), Nat. Biotechnol., 16: 642-646) and a ES cell production technique (supra) is used (Sayaka Wakayama et al., Experimental Medicine, vol. 26, No. 5 (extra issue), p. 47-52). For nuclear transplantation, reprogramming can be carried out by injecting the nucleus of a somatic cell into an enucleated unfertilized egg of a mammal and culturing the egg for several hours.

(F) Fused Stem Cell

An egg or ES cell fused with a somatic cell is a stem cell having pluripotency similar to an ES cell for fusion and further having genes characteristic of the somatic cell (Tada M. et al. Curr Biol. 11: 1553-8, 2001; Cowan C. A. et al. Science, 2005 Aug. 26; 309 (5739): 1369-73).

For the purpose of the present invention, the induction of differentiation from a pluripotent stem cell includes not only the induction of differentiation into a particular organ cell and its progenitor but also the induction of differentiation into a cell population containing a wide range of cell types, such as an entodermal cell, a mesodermal cell, and an ectodermal cell. Examples of the organ cell include, but not limited to, cells contained in the skin, blood vessel, cornea, kidney, heart, liver, umbilical cord, intestine, nerve, lung, placenta, pancreas, brain, peripheral extremities, retina, and the like. Any differentiation induction method obvious to one skilled in the art can be used. Examples thereof include a method for induction of differentiation into a neural stem cell as described in Japanese Patent Laid-Open No. 2002-291469 or International Publication No. WO2011/019092, a method for induction of differentiation into a pancreatic stem cell as described in Japanese Patent Laid-Open No. 2004-121165, a method for induction of differentiation into a hematopoietic cell as described in National Publication of International Patent Application No. 2003-505006, and a method for induction of differentiation into a myocardial cell as described in International Publication No. WO2014/185358. In addition, examples of a differentiation induction method using the formation of an embryoid body include a method as described in National Publication of International Patent Application No. 2003-523766.

The polyphenylalanine derivative of the present invention can be added to the culture medium of a cell population of interest to induce the cell death of pluripotent cells contained in the cell population of interest to remove the pluripotent cells. The time of contacting between the cell population of interest and the polyphenylalanine derivative is not particularly limited; however, it is, for example, 1 hour, 2 hours, 3 hours, 4 hours, 5 hours, 6 hours, 12 hours, or 24 hours. The concentration of the polyphenylalanine derivative in the culture medium is not particularly limited; it is, for example, 100 µM to 1 mM, preferably 200 µM, 300 µM, or 400 µM.

EXAMPLES

The present invention will be described below in further detail based on Examples. However, the scope of the invention is not to be limited to these Examples.

Example 1

<iPS Cell>

Human iPS cells (201B7) were given from Professor Yamanaka at Kyoto University (Takahashi K, et al. Cell. 131: 861-72, 2007) and were cultured by a method as described in Nakagawa, et al. Sci Rep. 4: 3594, 2014.

Human iPS cells (1231A3) were given from Professor Yamanaka at Kyoto University and were cultured by a method as described in Nakagawa, et al. Sci Rep. 4: 3594, 2014.

Human iPS cells (MYH6-EIP4-201B7) were prepared by introducing an EGFP cassette (MYH6-EIP4) operatively connected to MYH6 promoter into the 201B7. The MYH6-EIP4-introduced iPS cell line was prepared by introducing, into 201B7, a vector in which the EGFP cassette was operatively linked downstream of a MYH (myosin heavy chain)-promoter, using a PiggyBac transposon system.

<Myocardial Cell Line>

For a myocardial cell line, MYH6-EIP4-201B7 was treated with CTK solution (ReproCELL) for 2 minutes before removing the solution, subsequently treated with Accumax (Innovative Cell Technologies) for 5 minutes, and then detached into single cells by pipetting. The cells were recovered by centrifugation, transferred to a low-attachment 6-well dish (Corning), and cultured in 1.5 ml/well STEMPRO 34 (Invitrogen) containing 2 mM L-glutamine, 150 µg/mL transferrin, 50 µg/mL ascorbic acid (Sigma), $4 \times 10^{-4}$ M monothioglycerol (MTG), and 2 ng/mL BMP4 (R&D) under conditions of 37° C. and 5% oxygen to form EB. The following day, an equal amount of STEMPRO 34 containing 1% L-glutamine, 150 µg/mL transferrin, 50 µg/mL ascorbic acid, $4 \times 10^{-4}$M MTG, 18 ng/mL BMP4, 10 ng/mL bFGF, and 12 ng/mL Activin A was added to a 6-well plate in which EB were cultured, followed by culture under conditions of 37° C. and 5% oxygen for 3 days. The resultant EB were washed with IMDM (Invitrogen), and cultured under conditions of 37° C. and 5% oxygen for 4 days after adding, to the dish, STEMPRO 34 containing 1% L-glutamine, 150 µg/mL transferrin, 50 µg/mL ascorbic acid, $4 \times 10^{-4}$M MTG, 10 ng/mL VEGF, and 1 µM IWP-3. The medium was replaced with STEMPRO 34 containing 1% L-glutamine, 150 µg/mL transferrin, 50 µg/mL ascorbic acid, $4 \times 10^{-4}$M MTG, 10 ng/mL VEGF, and 5 ng/mL bFGF, followed by culture under conditions of 37° C. and 5% oxygen for 4 days. At this time, the medium was replaced with a medium having the same conditions every other day. Subsequently, culture was carried out at an ordinary concentration of oxygen for 8 days while replacing the medium with a medium having the same conditions every other day, and EGFP-positive cells were isolated by FACS using EGFP replacing MYH-6 as an index and used as a myocardial cell line.

<D-1 and D-3>

The compound having a structural formula of the following formula (IV) (where n=2) was used as compound D-1, and the compound having a structural formula of the following formula (IV) (where n=3) was used as compound D-3.

[Formula 8]

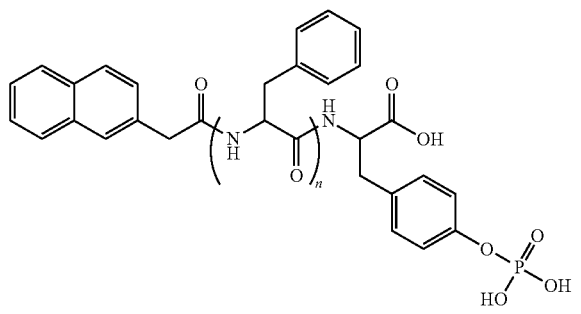

(IV)

D-1 and D-3 were prepared by a solid-phase peptide synthesis method as described in Ottinger, E. A., et al., Biochemistry, 32, 1993. Specifically, they were synthesized by activating 2-chlorotrityl chloride resin, N-Fmoc-protected amino acids, and 2-naphthaleneacetic acid using N,N-diisopropylethylamine (DIPEA) and O-benzotriazole-N,N,N',N'-tetramethyl-uronium-hexafluoro-phosphate (HBTU). O-phospho-D-tyrosine was synthesized by reacting D-tyrosine with phosphorus pentoxide a whole day and night in the presence of phosphoric acid according to a method as described in Alewood, P. F., et al., Synthesis, 30-31, 1983. N-Fmoc-O-phospho-D-tyrosine was obtained by dissolving O-phospho-D-tyrosine and Fmoc-OSu in a 1:1 mixed solvent of water and CH3CN, adding Et3N to adjust pH to 8 to 9, and reacting the solution for 30 minutes (Ottinger, E. A., et al., Biochemistry, 32, 1993).

Example 2

201B7 cells were seeded in Stemfit (Ajinomoto) containing Rock inhibitor on a laminin-coated 24-well plate to $2\times10^4$/well (24-well plate) (day 0). After 24 hours, the medium was replaced with a medium consisting of Stemfit alone, and culture was continued for 24 hours. Alternatively, $1\times10^4$/well (24-well plate) of a myocardial cell line was seeded and cultured in StemPro (Life Technologies) for 1 day. Subsequently, 0 μM, 200 μM, 300 μM, or 400 μM D-3 was added to the culture solution, which was then cultured for 1 hour or 2 hours. The medium was replaced with a D-3-free medium, and after 1 day of culture, cell death was evaluated by WST-1 assay to calculate the cell viability by comparison to that for addition of 0 μM D-3. As a result, when 300 μM or more D-3 was added to the culture solution, which was then cultured for 1 hour or more, 201B7 were determined to cause cell death (FIG. 1). On the other hand, for the myocardial cell line, no cytotoxicity due to D-3 was found.

The above-described results suggested that D-3 caused cell death specifically in pluripotent stem cells. Similarly, NHDF (normal human dermal fibroblasts) or 1-HS5 (normal human medullary stromal cells) were cultured for 1 hour or 2 hours by adding 0 μM, 200 μM, 300 μM, or 400 μM of D-3 to the culture solution. The medium was replaced with a D-3-free medium, and after 1 day of culture, cell death was evaluated by WST-1 assay to calculate the cell viability by comparison to that for addition of 0 μM D-3. As a result, cytotoxicity due to D-3 was not found against both types of cells.

Example 3

Figure 2:
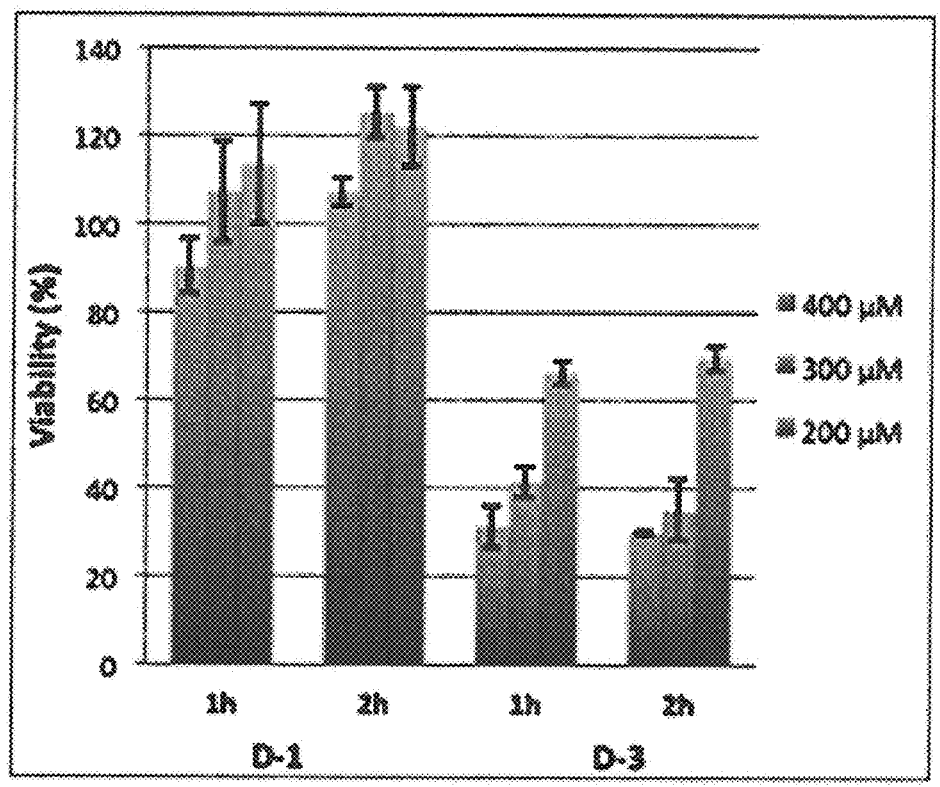
FIG. 2 is a pair of graphs showing the viability of 1231A3 cultured in Stemfit (upper) and DMEM (lower) for 1 day after contacting the cells with D-3 for 1 hour (1 h) or 2 hours (2 h). The ordinate represents, as cell viability, values calculated by setting each of the results of performing the same experiments without contacting with D-3 to 100%.
Figure 2:
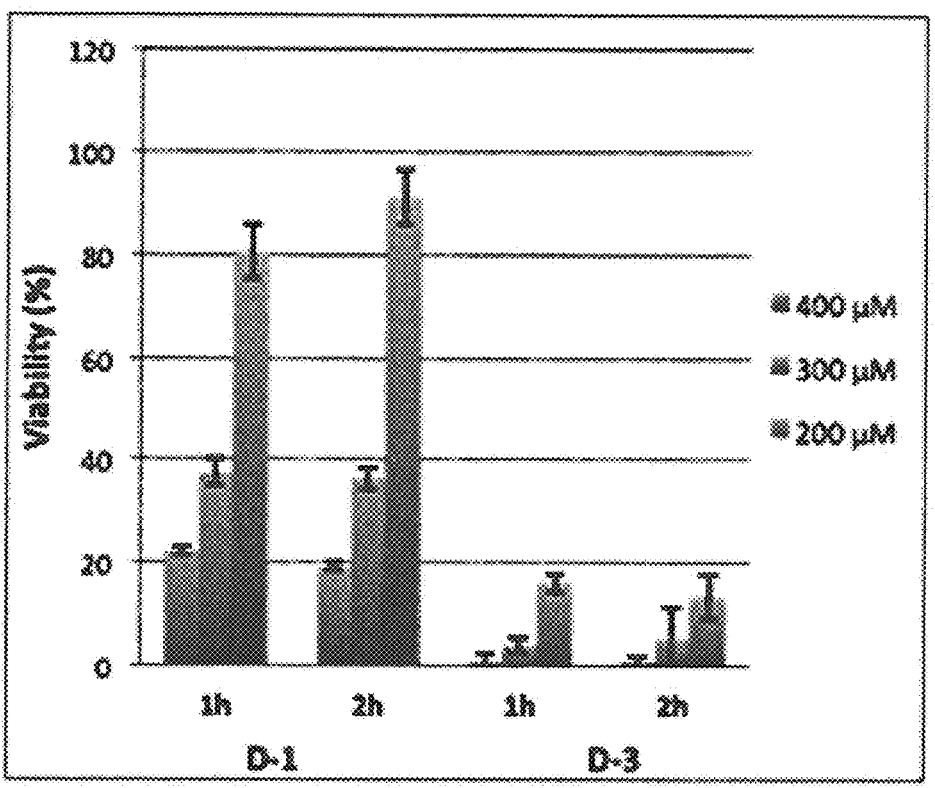

1231A3 cells were seeded in Stemfit (Ajinomoto) containing Rock inhibitor on a laminin-coated 24-well plate to $2\times10^4$/well (24 well plate) (day 0). After 24 hours, the cells were cultured in Stemfit or DMEM (Life Technologies) for 1 day. Then, 0 μM, 200 μM, 300 μM, or 400 μM D-1 or 0 μM, 200 μM, 300 μM, or 400 μM D-3 was added to the culture solution, which was then cultured for 1 hour or 2 hours. Subsequently, the medium was replaced with a D1- or D-3-free medium, and after 1 day of culture, each cell viability was calculated by WST-1 assay by comparison to that of the cells when D-1 or D-3 was not added (0 μM). As a result, it was determined that D-3 exerted toxicity against pluripotent stem cells without being affected by the medium (FIG. 2).

Example 4

Figure 3:
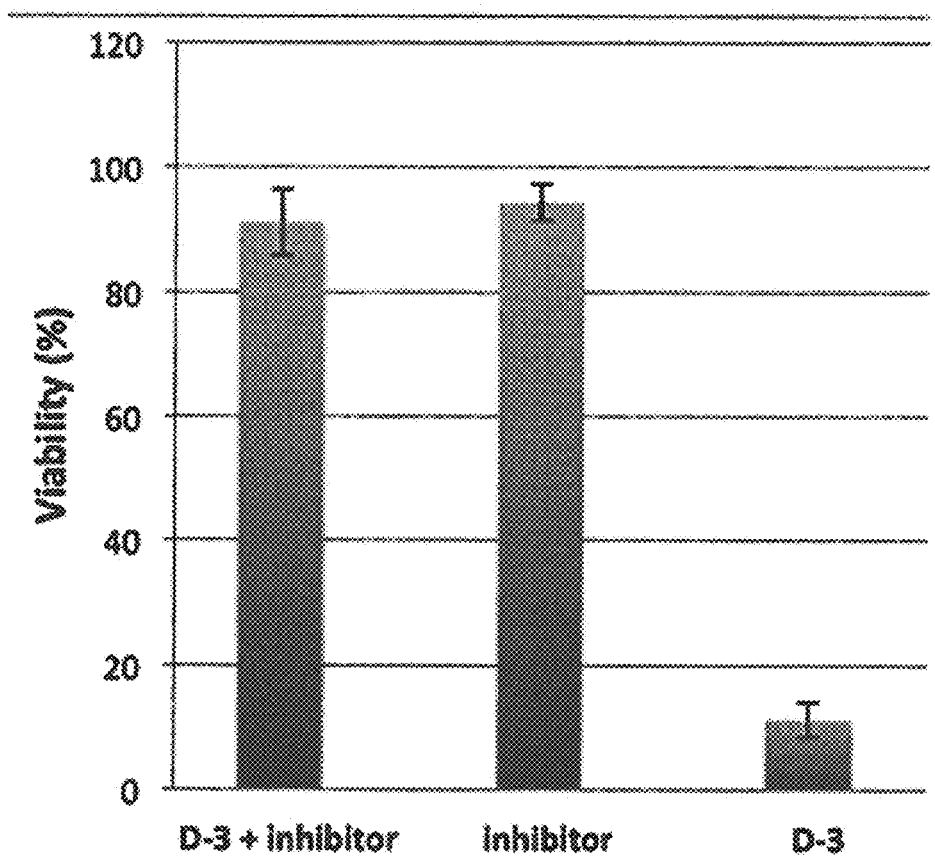
FIG. 3 is a pair of graphs showing the viability of 201B7 (upper) or 1231A3 (lower) cultured for 1 day after contacting the cells with a phosphatase inhibitor and D-3 (inhibitor+D-3), the phosphatase inhibitor, or D-3 for 1 hour (1 h). The ordinate represents, as cell viability, values calculated by setting each of the results of performing the same experiments without contacting with an agent to 100%.
Figure 3:
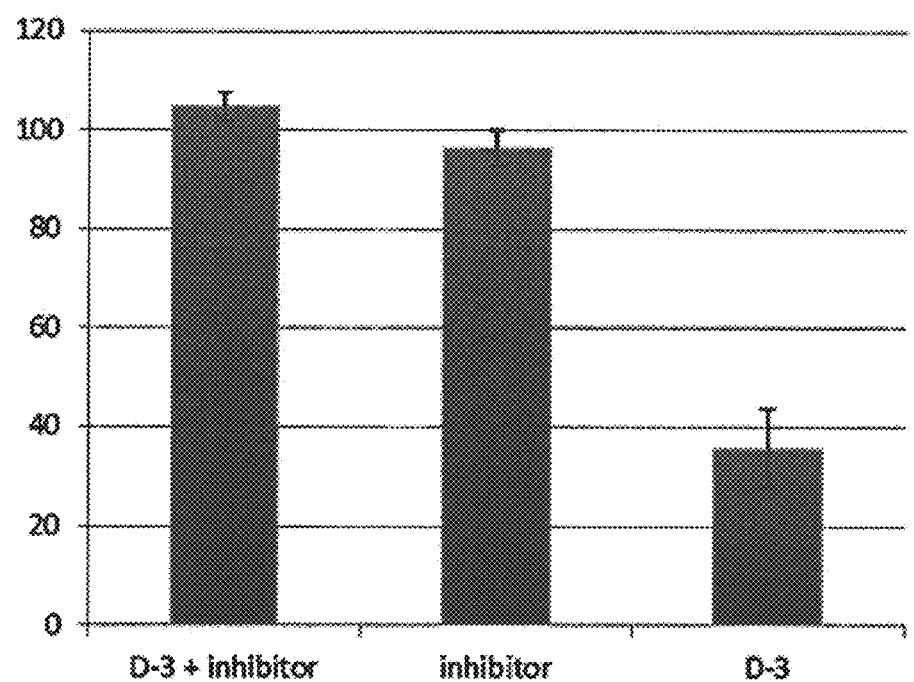

201B7 or 1231A3 cells were seeded in Stemfit (Ajinomoto) containing Rock inhibitor on a laminin-coated 24-well plate to $2\times10^4$/well (24-well plate) (day 0). After 24 hours, the medium was replaced with a medium consisting of Stemfit alone, and culture was continued for 24 hours. Subsequently, 0 μM or 400 μM D-3 and a phosphatase inhibitor (a mixture of 5 mM L-phenylalanine (Wakenyaku Co., Ltd.) and 2 mM L-homoarginine (Wakenyaku Co., Ltd.)) were added to the culture solution, which was then cultured for 1 hour or 2 hours. The medium was replaced with a D-3-free medium, and after 1 day of culture, cell death was evaluated by WST-1 assay to calculate the cell viability by comparison to that when D-3 and the phosphatase inhibitor were not added. As a result, it was suggested that cell death due to D-3 is mediated by phosphatase since the cytotoxicity of D-3 is suppressed by the phosphatase inhibitor (FIG. 3).

Example 5

Figure 4:
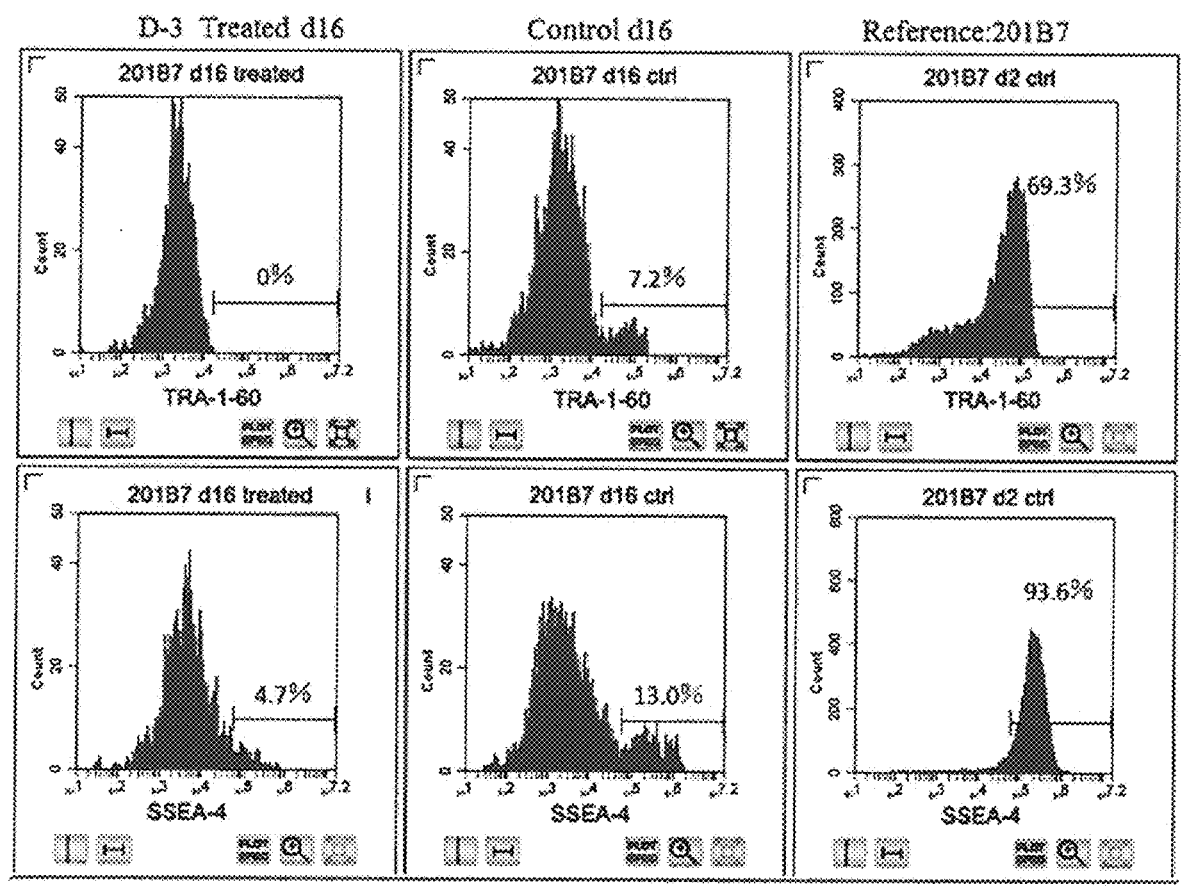
FIG. 4 is a series of histograms after staining cells with a TRA-1-60 antibody (upper) or an SSEA-4 antibody (lower). The left histograms show the results from cells obtained by inducing the differentiation of 201B7 (201B7d16) cultured for 1 day after contacting the cells with D-3 for 1 hour (1 h); the middle histograms show the results from cells obtained by inducing the differentiation of 201B7 (201B7d16); and the right histograms show the results from 201B7. In the histograms, the numbers indicate the content of TRA-1-60-positive cells (upper) or SSEA-4-positive cells (lower).

201B7 were spontaneously differentiated by culturing the cells in Stemfit containing no bFGF for 16 days. Subsequently, the cells were seeded in Stemfit (Ajinomoto) containing Rock inhibitor but not bFGF on a 24-well plate coated with laminin to $2\times10^4$/well (24-well plate) (day 0). After 24 hours, the medium was replaced with a medium consisting of Stemfit alone without containing bFGF, and culture was continued for 24 hours. Subsequently, 0 μM or 400 μM D-3 was added to the culture solution, which was then cultured for 1 hour. The medium was replaced with a D-3-free medium, and after 1 day of culture, the cells were separated and recovered and stained with an antibody to TRA-1-60 (BD Pharmingen) or SSEA4 (BD Pharmingen). For live cells not stained by 7-amino-actinomycin D (7-AAD), the content of TRA-1-60- or SSEA4-positive cells was evaluated using FACS. As a positive control, undifferentiated 201B7 were used. As a result, culture by adding D3 was demonstrated to remove or decrease TRA-1-60- or SSEA4-positive cells (FIG. 4).

Figure 5:
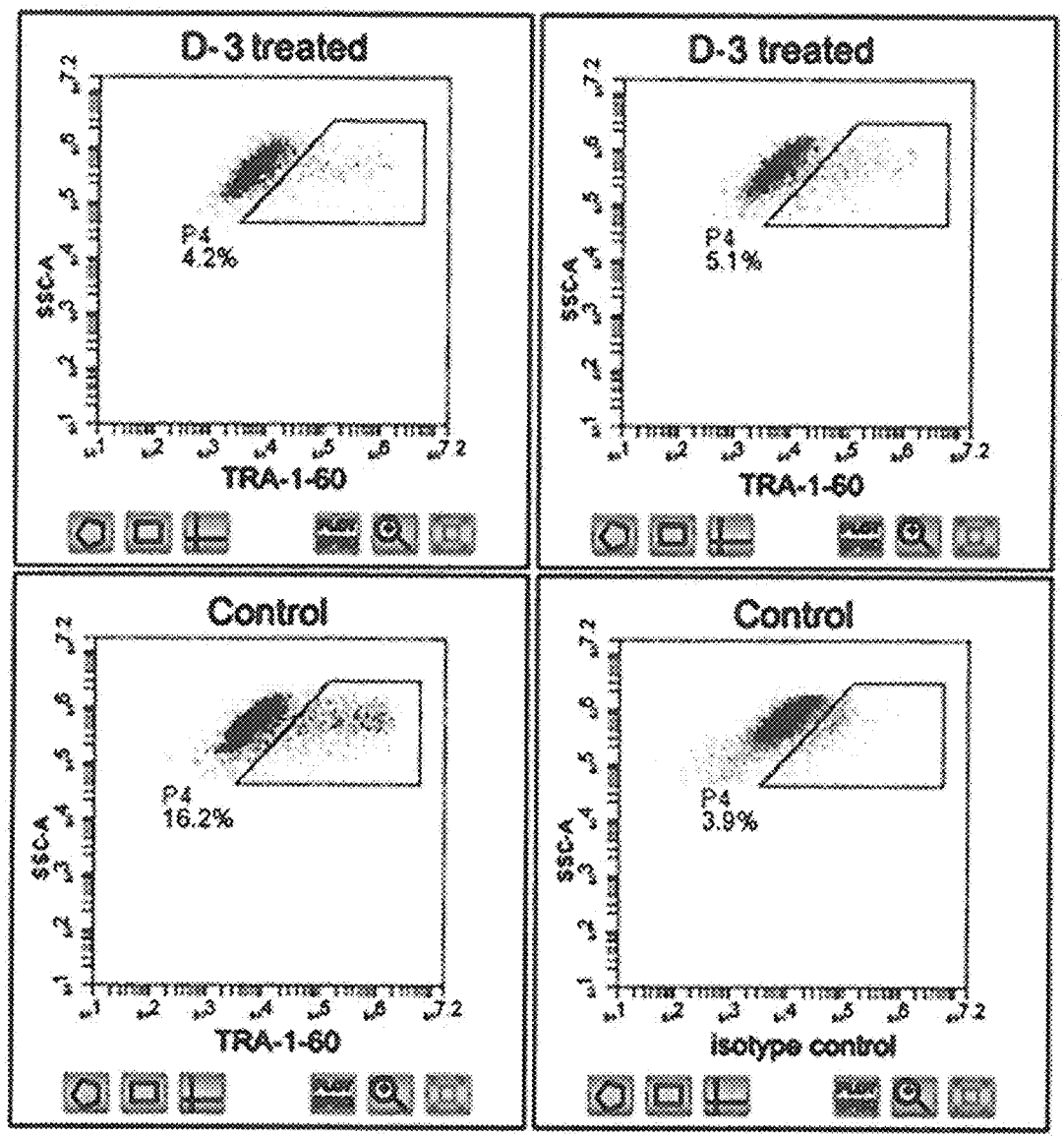
FIG. 5 is a series of graphs showing dot plots of the results of staining cells with a TRA-1-60 antibody and performing FACS measurement. In the figure, the upper graphs show the results from spontaneously differentiated 201B7 (201B7 were cultured in Stemfit for 16 days without adding bFGF) cultured for 23 hours after contacting the cells with D-3, and the lower graphs show the results from spontaneously differentiated 201B7 (201B7d16). The lower right graph shows the results of staining cells obtained by inducing the differentiation of 201B7 with IgG as an isotype control. In the graphs, the numbers indicate the content of TRA-1-60-positive cells (upper right, upper left, and lower left) and the content of the pseudo-positive cells (lower right).

Similarly, 201B7 were spontaneously differentiated by culturing the cells in Stemfit containing no bFGF for 16 days. Subsequently, the cells were seeded in Stemfit (Ajinomoto) containing Rock inhibitor but not bFGF on a 24-well plate coated with laminin to $2\times10^4$/well (24-well plate) (day 0). After 24 hours, the medium was replaced with a medium consisting of Stemfit alone without containing bFGF, and culture was continued for 24 hours. Subsequently, 0 μM (control) or 400 μM D-3 was added to the culture solution, which was then cultured for 1 hour. The medium was replaced with a D-3-free medium, and after 23 hours of culture, the cells were separated and recovered and stained with an antibody to TRA-1-60. For live cells not stained by 7-AAD, the content of TRA-1-60-positive cells was evaluated using FACS. At this time, a few non-specific positive cells were detected by staining with IgM, κ isotype (BD Pharmingen) as a negative control. As a result, as described above, culture by adding D-3 was demonstrated to remove or decrease TRA-1-60-positive cells (FIG. 5).

Example 6

Figure 6:
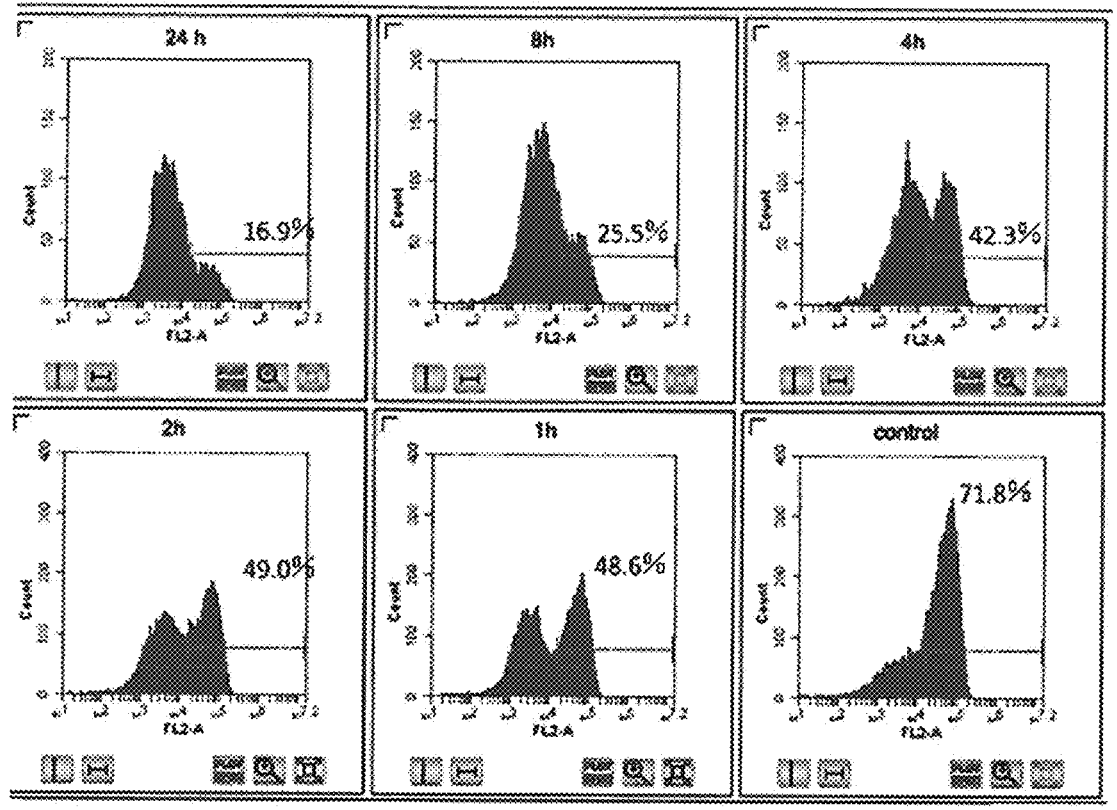
FIG. 6 is a series of histograms showing the results of staining a cell mixture of 201B7 and cells obtained by inducing the differentiation of 201B7 (201B7d16) cultured for 24 hours (24 h), 8 hours (8 h), 4 hours (4 h), 2 hours (2 h), or 1 hour (1 h) after contacting the cell mixture with D-3, or a cell mixture of 201B7 and 201B7d16 (control) with a TRA-1-60 antibody and performing FACS measurement. In the histograms, the numbers indicate the content of TRA-1-60-positive cells.

201B7 were spontaneously differentiated by culturing the cells in Stemfit containing no bFGF for 16 days. Then, $0.7 \times 10^5$ cells of 201B7 and $0.7 \times 10^5$ cells of spontaneously differentiated 201B7 were mixed and seeded in Stemfit (Ajinomoto) containing Rock inhibitor but not bFGF on a 6-well plate coated with laminin (day 0). After 24 hours, the medium was replaced with a medium consisting of Stemfit alone without containing bFGF, and culture was continued for 24 hours. Subsequently, culture was carried out in Stemfit containing 400 μM D-3 but not bFGF for 1 hour. The medium was replaced with a D-3-free medium, and culture was further carried out for 1 hour, 2 hours, 4 hours, 8 hours, or 24 hours. The cells after each culture were separated and recovered and stained with an antibody to TRA-1-60. For live cells not stained by 7-AAD, the content of TRA-1-60-positive cells was evaluated using FACS. As a positive control, used were cells obtained immediately after mixing 201B7 and cells differentiation-induced by culturing 201B7 in Stemfit not containing bFGF for 16 days. As a result, it was demonstrated that cell damage occurred from 1 hour after contact with D-3 and cell death of pluripotent stem cells occurred with the lapse of time (FIG. 6).

Figure 7:
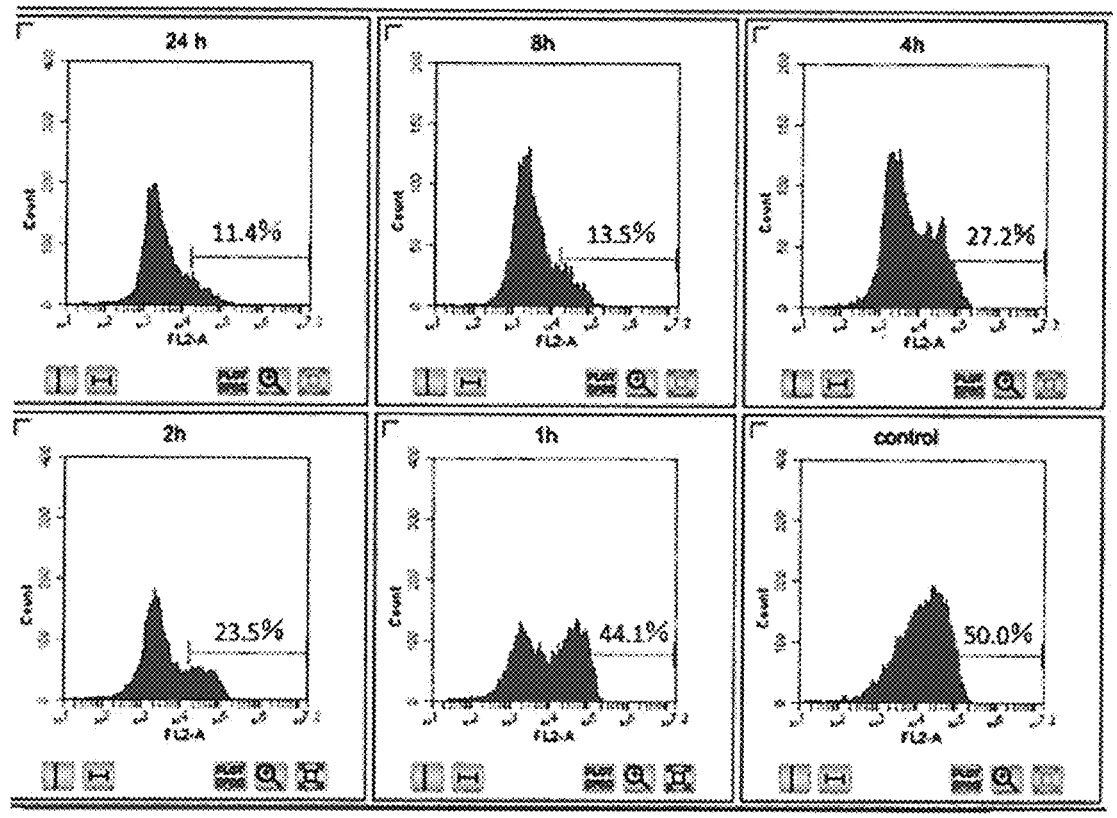
FIG. 7 is a series of histograms showing the results of staining a cell mixture of 1231A3 and cells obtained by inducing the differentiation of 1231A3 (1231A3d18) cultured for 24 hours (24 h), 8 hours (8 h), 4 hours (4 h), 2 hours (2 h), or 1 hour (1 h) after contacting the cells with D-3, or a cell mixture of 201B7 and 1231A3d18 (control) with a TRA-1-60 antibody and performing FACS measurement. In the histograms, the numbers indicate the content of TRA-1-60-positive cells.

Similarly, 1231A3 were spontaneously differentiated by culturing the cells in Stemfit containing no bFGF for 16 days. Then, $0.5 \times 10^5$ cells of 1231A3 and $0.7 \times 10^5$ cells of spontaneously differentiated 201B7 were mixed and seeded in Stemfit (Ajinomoto) containing Rock inhibitor but not bFGF on a 6-well plate coated with laminin (day 0). After 24 hours, the medium was replaced with a medium consisting of Stemfit alone without containing bFGF, and culture was continued for 24 hours. Subsequently, culture was carried out in Stemfit containing 400 μM D-3 but not bFGF for 1 hour. The medium was replaced with a D-3-free medium, and culture was further carried out for 1 hour, 2 hours, 4 hours, 8 hours, or 24 hours. The cells after each culture were separated and recovered and stained with an antibody to TRA-1-60. For live cells not stained by 7-AAD, the content of TRA-1-60-positive cells was evaluated using FACS. As a positive control, used were cells obtained immediately after mixing 1231A3 and cells differentiation-induced by culturing 1231A3 in Stemfit not containing bFGF for 18 days. As a result, it was demonstrated that cytotoxicity occurred from after contact with D-3 and cell death of pluripotent stem cells occurred with the lapse of time (FIG. 7).

Figure 8:
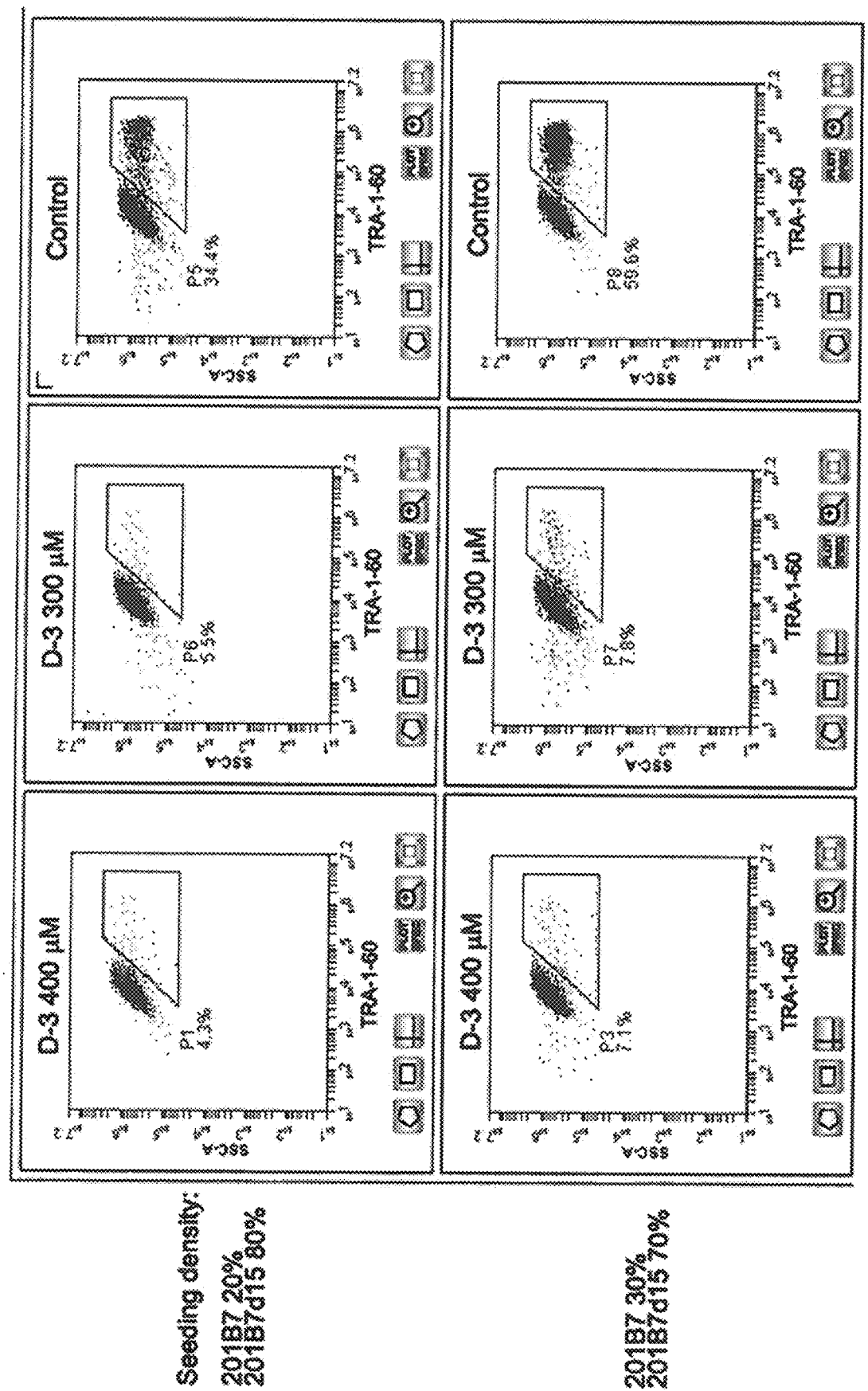
FIG. 8 is a series of graphs showing dot plots of the results of staining a 2:8 (upper) or 3:7 (lower) cell mixture of 201B7 and cells obtained by inducing the differentiation of 201B7 (201B7d16) contacted with 400 μM (left graphs) or 300 μM (middle graphs) D-3 or non-contacted (control) with D-3 (right graphs) with a TRA-1-60 antibody and performing FACS measurement. In the graphs, the numbers indicate the content of TRA-1-60-positive cells.

Similarly, 201B7 were spontaneously differentiated by culturing the cells in Stemfit containing no bFGF for 16 days. Then, 201B7 and the spontaneously differentiated 201B7 were mixed at 2:8 or 3:7 and seeded in Stemfit (Ajinomoto) containing Rock inhibitor but not bFGF on a 6-well plate coated with laminin (day 0). After 24 hours, the medium was replaced with a medium consisting of Stemfit alone without containing bFGF, and culture was continued for 24 hours. Subsequently, culture was carried out in Stemfit containing 0 μM, 300 μM, or 400 μM D-3 but not bFGF for 1 hour. The medium was replaced with a D-3-free medium, and culture was further carried out for 23 hours. The cells after each culture were separated and recovered and stained with an antibody to TRA-1-60. For live cells not stained by 7-AAD, the content of TRA-1-60-positive cells was evaluated using FACS. As a result, contact with D-3 was demonstrated to result in the occurrence of cell death selective for TRA-1-60-positive cells (FIG. 8).

Example 7

Figure 9:
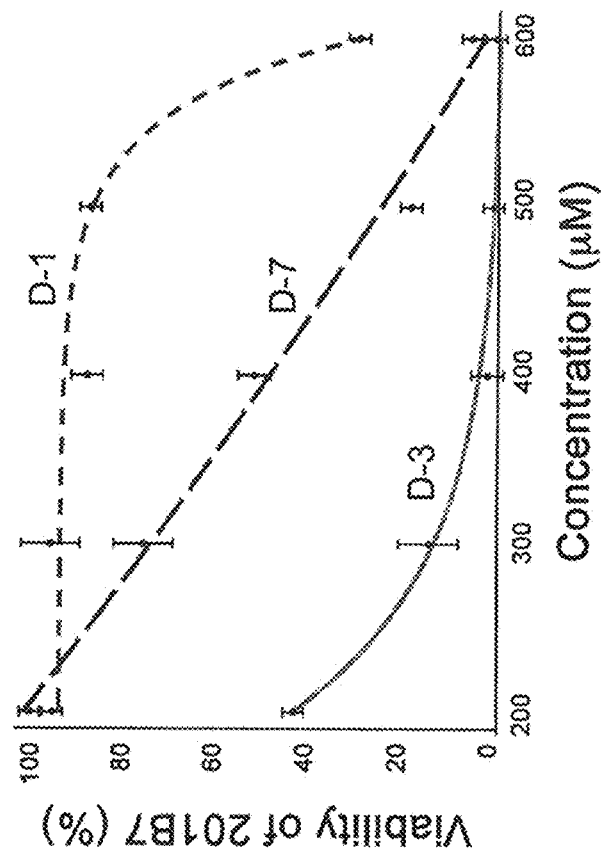
FIG. 9 is a graph showing the results of evaluating the anti-iPS cell effect of a diphenylalanine-based phosphor D peptide. D-1 has two phenylalanine moieties, and D3 has three phenylalanine moieties. D-7 further has a glycine residue providing a linker between the naphthyl group and the triphenylalanine moieties in D-3.
Figure 9:
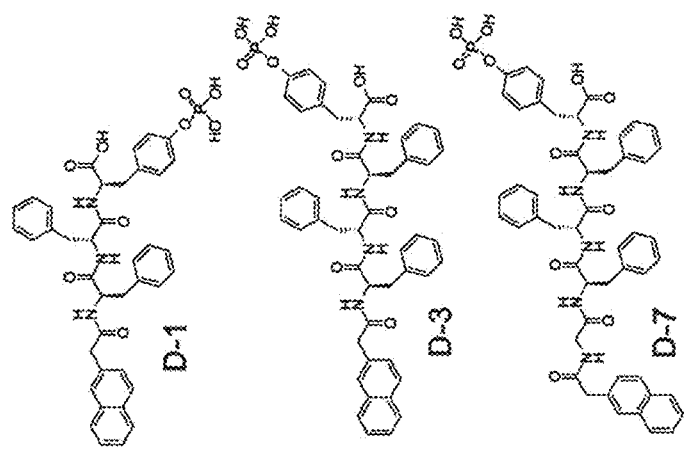

201B7 were seeded in Stemfit containing Rock inhibitor on a 24-well plate coated with laminin to $2.6 \times 10^4$ cells/cm². After 24 hours, the medium was replaced with a medium consisting of Stemfit alone, and culture was continued. After further 24 hours, the medium was replaced with Stemfit containing each of D-1, D-3, and D-7 molecules in different concentrations or Stemfit as a control. After 2 hours of culture, the medium was replaced with a medium consisting of Stemfit alone. The following day, the cells were collected using 100 μL of Accumax. Then, 300 μL of Stemfit was added to stop the Accumax reaction. The number of live cells in 100 μL of each sample was measured using flow cytometry. Before analysis for discriminating dead cells, 7-AAD was added to the each sample. As a result, not only the use of D-3 but also the use of D-1 or D-7 was shown to be capable of causing the cell death of 201B7 (FIG. 9).

Example 8

Figure 10:
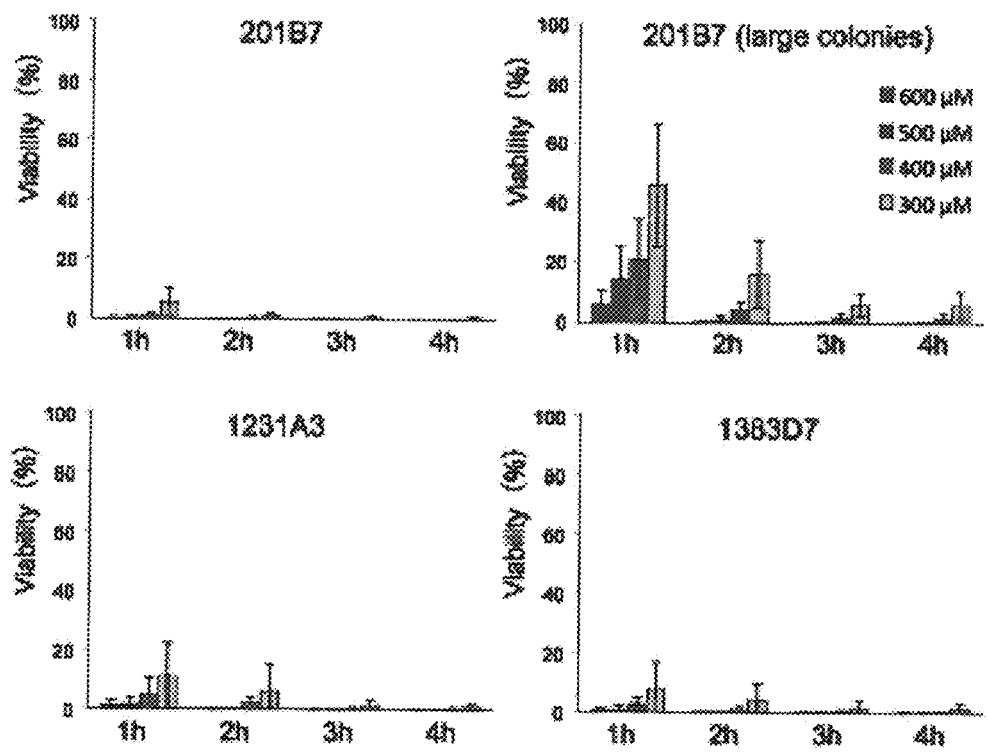
FIG. 10 is a series of graphs showing lethality when 3 iPS cell lines (201B7, 1231A, and 1383D7) were treated with different concentrations of D-3 for 1 to 4 hours. The upper 2 panels compare toxicity against 201B7 different in the cell concentration and different in the colony size.

Three types of iPS cell lines (201B7, 1231A, and 1383D7) were each seeded in Stemfit containing Rock inhibitor on a 24-well plate coated with laminin to $2.6 \times 10^4$ cells/cm². 201B7 were also seeded to $5.3 \times 10^4$ cells/cm² and thereby a sample forming large colonies was prepared. Human iPS cells (1383D7) were used by culturing those given from Dr. Asuka Morizane at Kyoto University. After 24 hours, the medium was replaced with a medium consisting of Stemfit alone, and culture was continued. After further 24 hours, the medium was replaced with Stemfit containing D-3 at different concentrations, or Stemfit as a control. After 1 to 4 hours of culture, the medium was replaced with a medium consisting of Stemfit alone. The following day, the cells were collected using 100 μL of Accumax. Then, 300 μL of Stemfit was added to stop the Accumax reaction. The number of live cells in 100 μL of each sample was measured using flow cytometry. Before analysis for discriminating dead cells, 7-AAD was added to the each sample. As a result, the addition of D-3 was shown to be capable of causing the cell death of all of the iPS cell lines 201B7, 1231A, and 1383D7 (FIG. 10). For the same cell line, the efficiency of cell death due to D-3 of 201B7 seeded at a low concentration was found to be higher than that for 201B7 seeded at a high concentration to form larger colonies. The efficiency is probably strongly affected by the contact area between D-3 and the cells since the non-contact area between D-3 and the cells occurs for high concentration seeding.

Example 9

Figure 11:
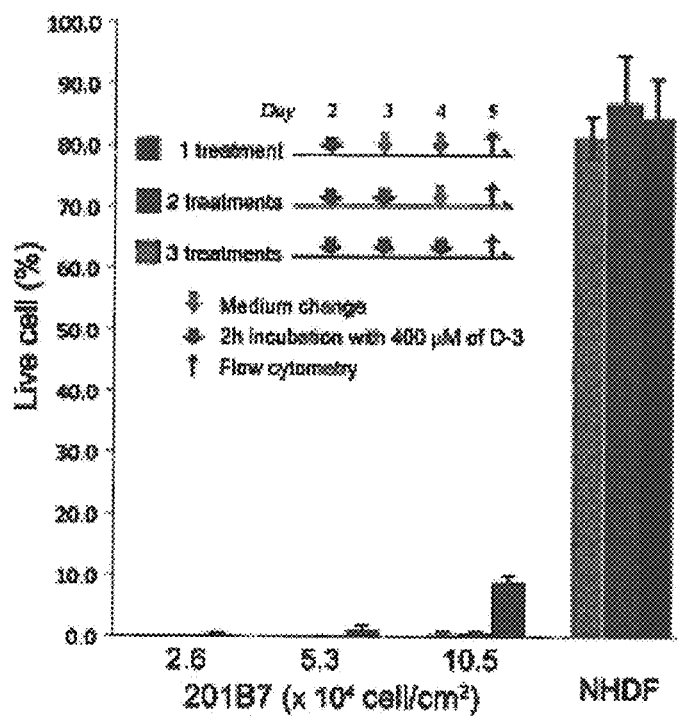
FIG. 11 is a graph showing that repetitive treatment with D-3 can remove 201B7 at a near-confluent stage. The graph shows the viability of 201B7 after treatment with D-3 on each day, compared to a control in which the medium was replaced on a daily basis. 201B7 were seeded at different concentrations, thereby forming small colonies, large colonies, and a near-confluent stage. NHDF cells were used as a control and subjected to the same D-3 treatment on a daily basis.

201B7 cells were seeded in Stemfit containing Rock inhibitor on a 24-well plate coated with laminin to $2.6 \times 10^4$ cells/cm², $5.3 \times 10^4$ cells/cm², or $10.5 \times 10^4$ cells/cm² (day 0). After 24 hours, the medium was replaced with a medium consisting of Stemfit alone, and culture was continued. After further 24 hours, the medium was replaced with Stemfit containing D-3 at a concentration of 400 μM. After 2 hours of culture, the medium was replaced with a medium consisting of Stemfit alone. The cells were treated once (only at day 2), two times (at day 2 and day 3), or three times (at days 2 to 4) with D-3. Then, the cells were collected using 100 µL of Accumax at day 5, and 300 µL of Stemfit was added thereto to stop the Accumax reaction. The number of live cells in 100 µL of each sample was measured using flow cytometry. Before analysis for discriminating dead cells, 7-AAD was added to the each sample. NHDF were seeded in FGM fibroblast medium on a 24-well plate to $5.3 \times 10^4$ cells/cm$^2$. The cells were treated at days 2 to 4 by incubation with 400 µM D-3 in FGM fibroblast medium for 2 hours. Then, the cells were collected at day 5 by the same method as that for the 201B7 cells; the Accumax reaction was stopped; and the number of live cells in 100 µL of each sample was similarly measured using flow cytometry. Before analysis for discriminating dead cells, 7-AAD was added to the each sample. As a result, it was found that repetitive treatment with D-3 could remove 201B7 even at a near-confluent stage with high accuracy (FIG. 11).

Example 10

Figure 12:
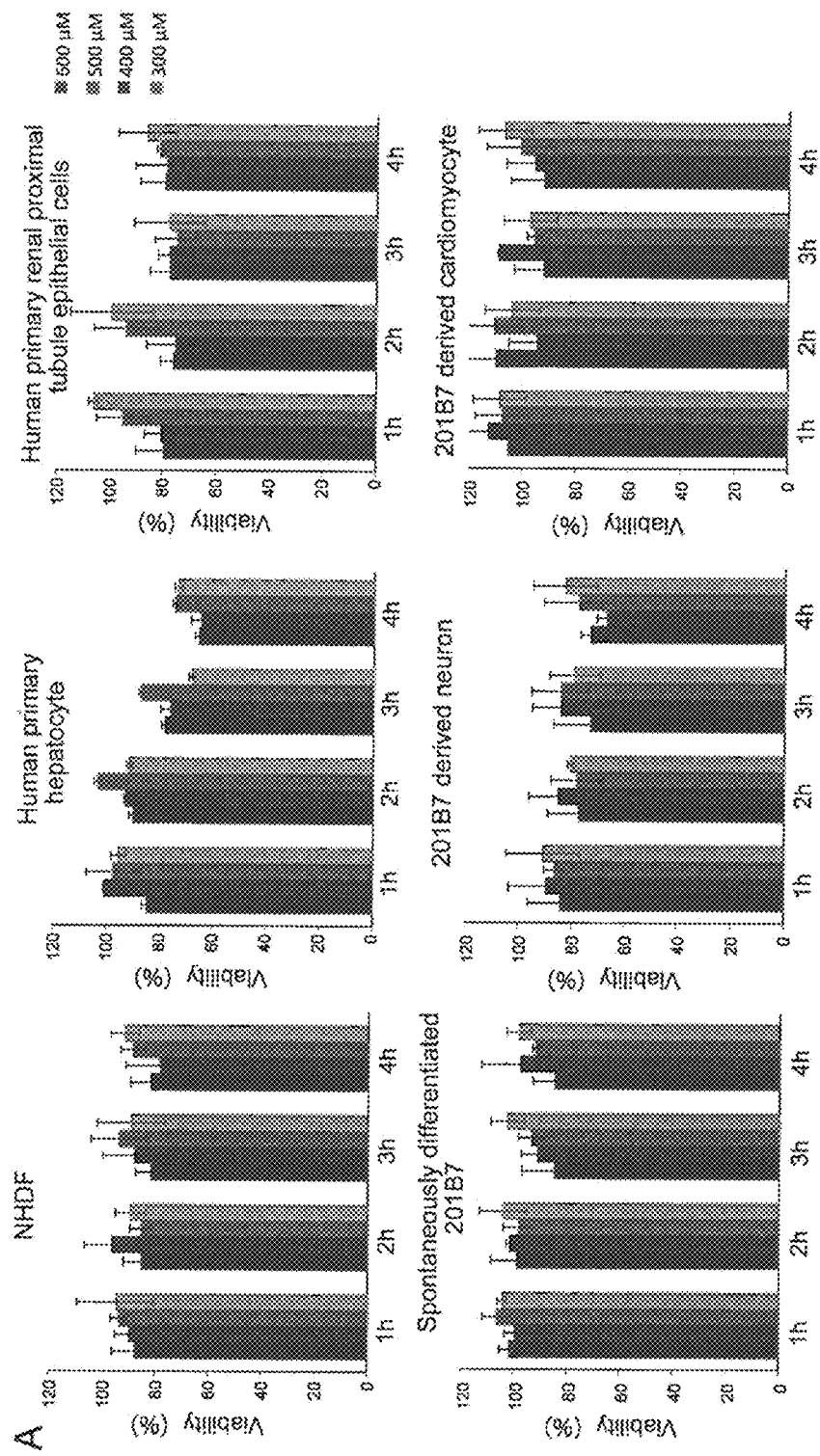
FIG. 12 is a series of graphs showing that D-3 is slightly toxic to normal dermal fibroblasts (NHDF), human primary hepatocytes, human primary renal proximal tubular epithelial cells, spontaneously differentiated 201B7, 201B7-derived nerve cells, and 201B7-derived myocardial cells as non-iPS cells.

Normal dermal fibroblasts (NHDF) were purchased from ATCC (American Type Culture Collection). Human primary hepatocytes and a hepatocyte medium were purchased from Cosmo Bio. Human primary renal proximal tubular epithelial cells and REGM™ BulletKit medium were purchased from Lonza. Spontaneously differentiated 201B7 were prepared by culturing 201B7 in Stemfit not containing bFGF for 2 weeks. 201B7-derived nerve cells were prepared according to the method described in the above-mentioned paper [Nakagawa, et al. Sci. Rep. 4: 3594, 2014]. 201B7-derived myocardial cells were prepared by the previously described method. All cells were maintained at 37° C. and 5% $CO_2$. These types of cells were seeded in the respective media on 24-well plates to $5.3 \times 10^4$ cells/cm$^2$. After 24 hours, the medium was replaced with each of media containing the D-3 molecule at different concentrations or the medium alone as a control. After 1 to 4 hours of culture, it was replaced with the medium alone. The following day, the cells were collected using 100 µL of Accumax. Then, 300 µL of Stemfit was added to stop Accumax reaction. The number of live cells in 100 µL of each sample was measured using flow cytometry. Before analysis for discriminating dead cells, 7-AAD was added to the each sample. As a result, it was shown that D-3 had little toxicity against various cells being not iPS cells (FIG. 12).

Figure 13:
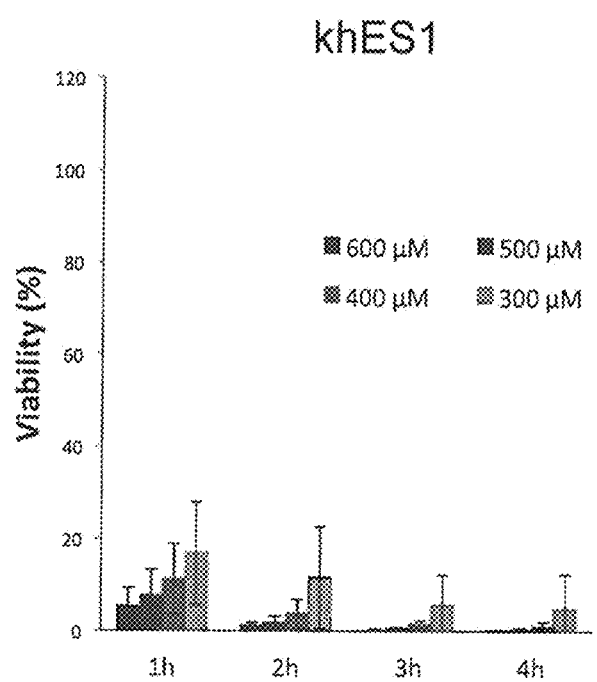
FIG. 13 is a graph showing that D-3 is also toxic to human ES cells (khES1).

Example 11 khES1 were used by culturing those given from Dr. Yoshinori Yoshida at Kyoto University. The toxicity of D-3 against khES1 was examined in the same way as that described in Example 8 except for seeding khES1 to $5.3 \times 10^4$ cells/cm$^2$. As a result, it was shown that D-3 was also toxic to the human ES cells (khES1) (FIG. 13).

Example 12

Figure 14:
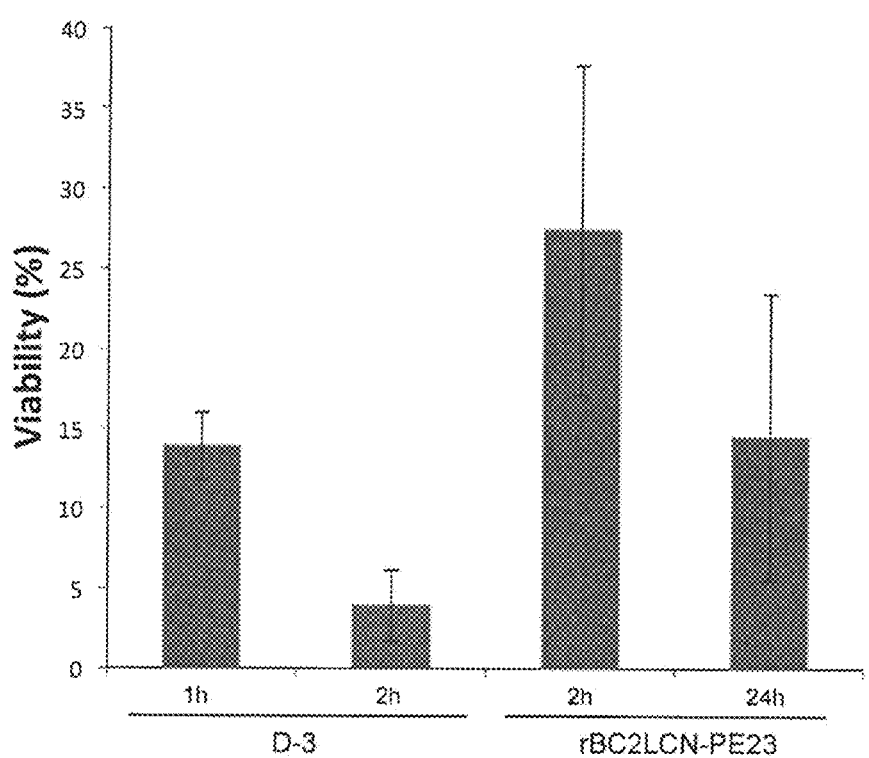
FIG. 14 is a graph comparing the toxicities of D-3 and rBC2LCN-PE23 as a commercial anti-iPS cell substance against 201B7, showing that D-3 has a higher efficacy than rBC2LCN-PE23.

An iPS cell line (201B7) was seeded in Stemfit containing Rock inhibitor on a 24-well plate coated with laminin to $5.3 \times 10^4$ cells/cm$^2$. After 24 hours, the medium was replaced with a medium consisting of Stemfit alone, and culture was continued. After further 24 hours, the medium was replaced with Stemfit containing D-3 at 400 µM, Stemfit containing rBC2LCN-PE23 at 10 µg/mL, or Stemfit as a control. The medium was replaced with a medium consisting of Stemfit alone after 1 or 2 hours of culture for D-3 and after 2 or 24 hours of culture for rBC2LCN-PE23. The following day, the cells were collected using 100 µL of Accumax. Then, 300 µL of Stemfit was added to stop Accumax reaction. The number of live cells in 100 µL of each sample was measured using flow cytometry. Before analysis for discriminating dead cells, 7-AAD was added to the each sample. As a result, it was shown that D-3 has a higher efficacy than rBC2LCN-PE23 as a commercial anti-iPS cell substance (FIG. 14). D-3 not only has a high effect of removing iPS cells but also enables the shortening of the treatment time for removal. D-3, which is a short peptide molecule, is also excellent in terms of being capable of being economically and easily synthesized in a large amount.

Example 13

Figure 15:
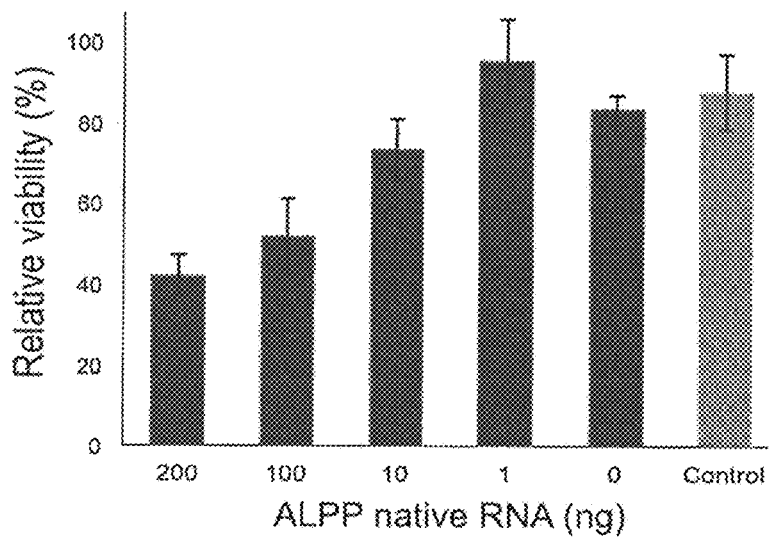
FIG. 15 is a graph showing that the toxicity of D-3 is associated with the amount of P-ALP mRNA introduced into cells (ALPP in FIG. 15 represents the same as P-ALP).

293FT were purchased from Invitrogen. 293FT were seeded in DMEM medium (10% FBS, 1% non-essential amino acids) on a 24-well plate to $5.3 \times 10^4$ cells/cm$^2$. After 24 hours, 293FT were transfected with wild-type placental alkaline phosphatase mRNA (P-ALP mRNA) at different concentrations using Stemfect reagent according to a standard protocol. After 4 hours, the medium was replaced with the culture medium alone. As a control, 293FT were used for which without treatment with D-3, only medium replacement was carried out in the same timed relation as that for the treatment. After 24 hours, the medium was replaced with each of those containing D-3 at different concentrations, and replaced with the medium alone for control. After 1 hour of culture, the medium was replaced with a medium consisting of Stemfit alone. The following day, the cells were collected using 100 µL of Accumax. Then, 300 µL of Stemfit was added to stop Accumax reaction. The number of live cells in 100 µL of each sample was measured using flow cytometry. Before analysis for discriminating dead cells, 7-AAD was added to the each sample. As a result, it was shown that the toxicity of D-3 was associated with the transfection amount of P-ALP mRNA (FIG. 15).

Example 14

Figure 16:
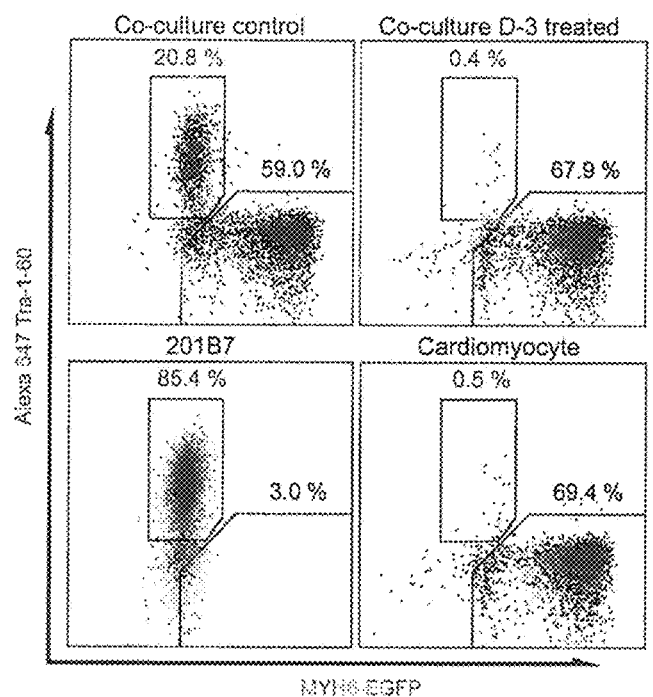
FIG. 16 is a series of graphs showing the successful removal of iPS cells mixed in a differentiated cell group. 201B7 and 201B7-derived myocardial cells expressing MHY6-EGFP were subjected to flow cytometric analysis after 1 hour culture using 400 µM D-3 or without performing such culture. The untreated 201B7 and the untreated myocardial cells were used as controls.

201B7 and 201B7-derived myocardial cells expressing MHY6-EGFP were seeded in Rock inhibitor-containing Stemfit on a laminin-coated 24-well plate so that the ratio of the numbers of the cells was 1:9 and the number of the cells totals $5.3 \times 10^4$ cells/cm$^2$. After 24 hours, the medium was replaced with Stemfit containing a suspension of 201B7-derived myocardial cells expressing MHY6-EGFP. After a further 24 hours, the medium was replaced with Stemfit containing D-3 at a concentration of 400 µM, and replaced with a medium consisting of Stemfit alone for a control. After 1 hour of culture, the medium was replaced with the medium consisting of Stemfit alone. The following day, the cells were collected using 100 µL of Accumax. Then, 400 µL of Stemfit was added to stop Accumax reaction. The number of live cells in 100 µL of each sample was measured using flow cytometry. Before analysis for discriminating dead cells, 7-AAD was added to the each sample. To discriminate 201B7, a Tra-1-60 antibody comprising Alexa 647 fluorophore was used. Myocardial cells at 20 days or 21 days after differentiation were sorted by selecting EGFP-positive cells. As a result, it was shown that the use of D-3 enabled the removal of iPS cells from a differentiated cell group (FIG. 16).

Example 15

Figure 17:
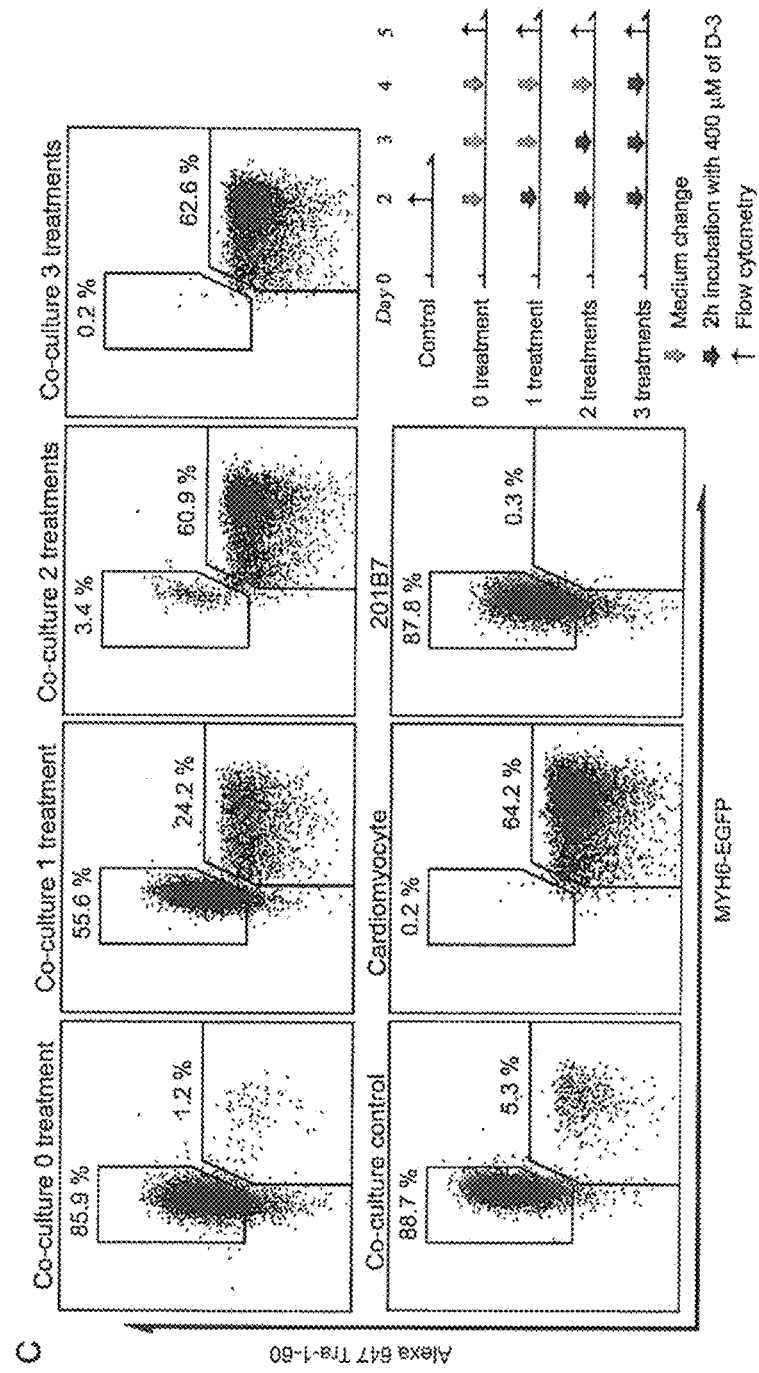
FIG. 17 is a series of graphs showing that repetitive treatment with D-3 resulted in success in purifying a small amount of differentiated cells from a cell group containing a large amount of iPS cells and the small amount of differentiated cells.

201B7 and 201B7-derived myocardial cells expressing MHY6-EGFP were each seeded in Rock inhibitor-containing Stemfit on a laminin-coated 24-well plate so that the ratio of the numbers of the cells was 7:3 and the number of the cells totals $5.3 \times 10^4$ cells/cm$^2$ (day 0). After 24 hours, the medium was replaced with Stemfit containing a suspension of 201B7-derived myocardial cells expressing MIHY6-EGFP (day 1). After further 24 hours, the medium was replaced with Stemfit containing D-3 at a concentration of 400 μM, and replaced with a medium consisting of Stemfit alone for a control. After 2 hours of culture, the medium was replaced with the medium consisting of Stemfit alone. The cells were treated once (only at day 2), two times (at day 2 and day 3), or three times (at days 2 to 4) with D-3. The following day, the cells were collected using 100 μL of Accumax. Then, 300 μL of Stemfit was added to stop Accumax reaction. The number of live cells in 100 μL of each sample was measured using flow cytometry. Before analysis for discriminating dead cells, 7-AAD was added to the each sample. To discriminate 201B7, a Tra-1-60 antibody comprising Alexa 647 fluorophore was used. Myocardial cells at 20 days or 21 days after differentiation were sorted by selecting EGFP-positive cells. As a result, it was shown that a small amount of differentiated cells were successfully purified from a cell group containing a large amount of iPS cells and the small amount of differentiated cells by use of D-3 (FIG. 17).

Example 16

Figure 18:
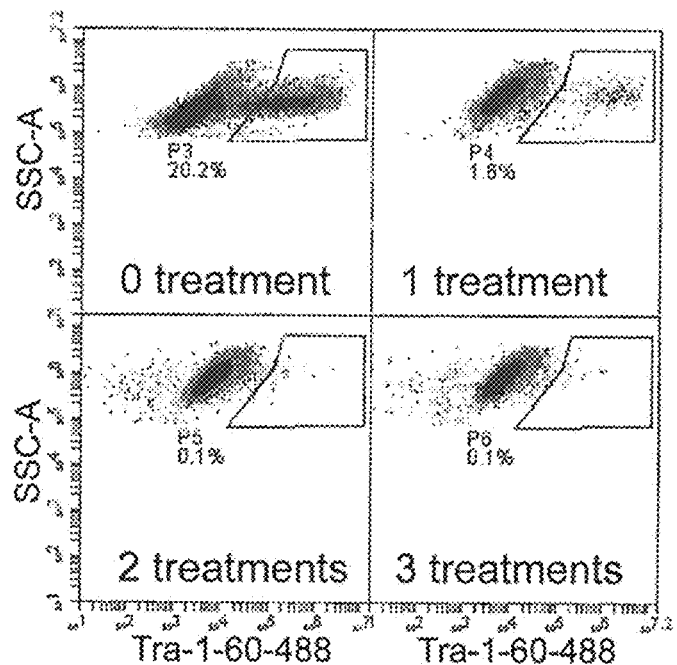
FIG. 18 is a series of graphs showing that from a differentiation-deficient clone of 201B7 spontaneously differentiated for 15 days, the remaining iPS cells were successfully removed using D-3.

A spontaneous differentiation-deficient clone of 201B7 was used and cultured in bFGF-free Stemfit to induce spontaneous differentiation. At day 15, the cells were seeded in Stemfit containing Rock inhibitor on a laminin-coated 24-well plate to $5.3 \times 10^4$ cells/cm$^2$ (day 0). After 24 hours, the medium was replaced with Stemfit. After a further 24 hours, the medium was replaced with Stemfit containing D-3 at 400 μM, or Stemfit as a control. After 2 hours of culture, the medium was replaced with the medium consisting of Stemfit alone. The cells were treated once (only at day 2), two times (at day 2 and day 3), or three times (at days 2 to 4). Then, at day 5, the cells were collected using 100 μL of Accumax, and 300 μL of Stemfit was added thereto to stop Accumax reaction. The number of live cells in 100 μL of each sample was measured using flow cytometry. Before analysis for discriminating cell death, 7-AAD was added to the each sample. To discriminate 201B7, a Tra-1-60 antibody comprising Alexa 647 fluorophore was used. As a result, it was shown that the use of D-3 enabled the removal of remaining iPS cells from a cell population derived from differentiation-deficient 201B7-derived iPS cells when spontaneous differentiation was induced for 15 days (FIG. 18).

Example 17

Figure 19:
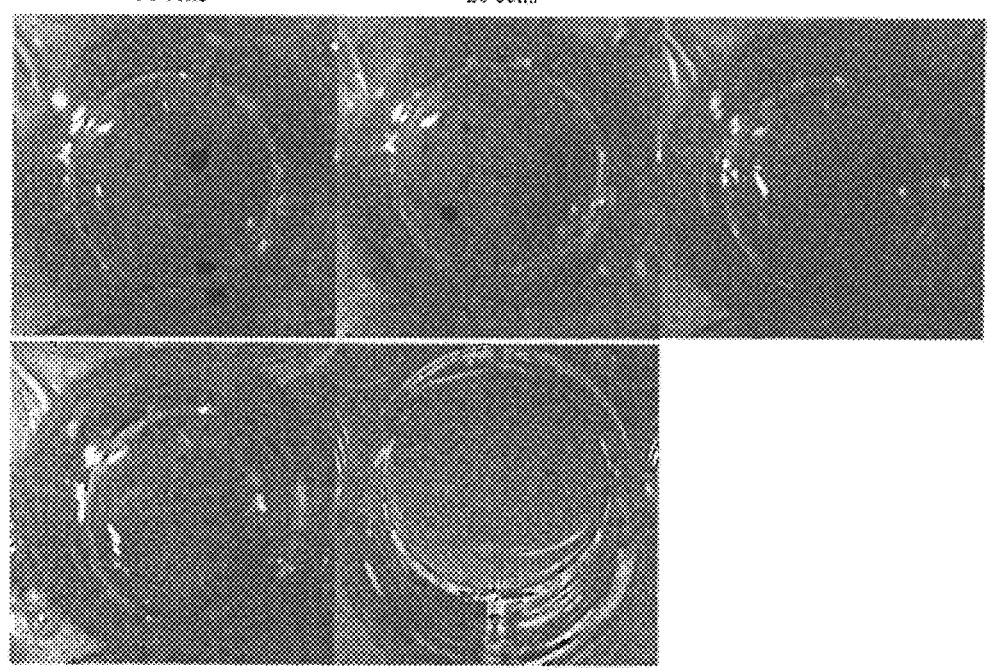
FIG. 19 is a series of photographs showing that from a co-culture of iPS cells and differentiated cells, the remaining iPS cells were successfully removed with D-3; staining indicating the presence of iPS cells can be visually identified in the upper left and upper middle panels representing a specimen not treated with D-3 and containing iPS cells, and the presence of iPS cells cannot be identified in the lower left and lower right panels representing a specimen treated with D-3 and the upper right panel representing no contained iPS cells.

$5 \times 10^4$ Cells of spontaneously differentiated 201B7 were mixed with 50 cells, 20 cells, or 0 cells of 201B7 and seeded in Stemfit (Ajinomoto) containing Rock inhibitor on a laminin-coated 24-well plate (day 0). After 24 hours, the medium was replaced with Stemfit (day 1). After further 24 hours, the medium was replaced with Stemfit containing D-3 at 400 μM, or Stemfit as a control (day 2). After 2 hours of culture, the medium was replaced with the medium consisting of Stemfit alone. Then, the cells were further cultured in Stemfit for 7 days. Colonies of 201B7 were stained reddish violet by ALP staining. As a result, it was shown that the use of D-3 enabled the removal of remaining iPS cells from a co-culture of iPS cells and differentiated cells (FIG. 19).

The invention claimed is:

1. An in vitro method for removing pluripotent cells, comprising a step of contacting a compound represented by formula (I);

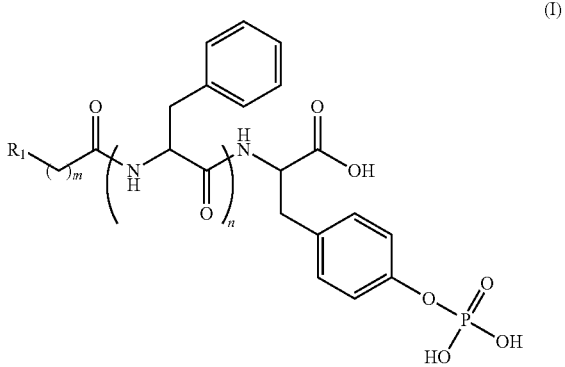

(I)

wherein $R_1$ represents, a naphthyl group; m represents 1; and n represents 2 or 3, or formula (II):

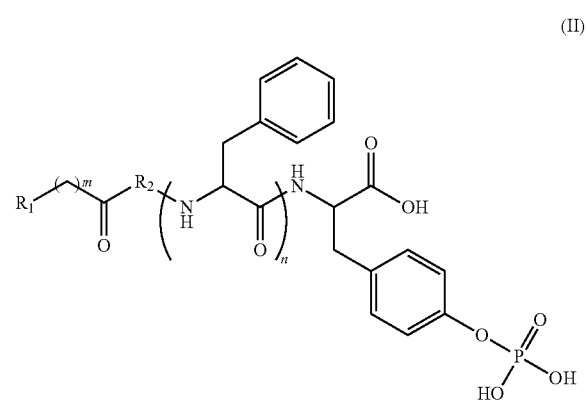

(II)

wherein $R_1$ represents, a naphthyl group; $R_2$ represents a glycine residue; m represents 1; and represents 3, with a cell population containing pluripotent cells and cells differentiated from pluripotent cells.

2. A compound represented by formula (I):

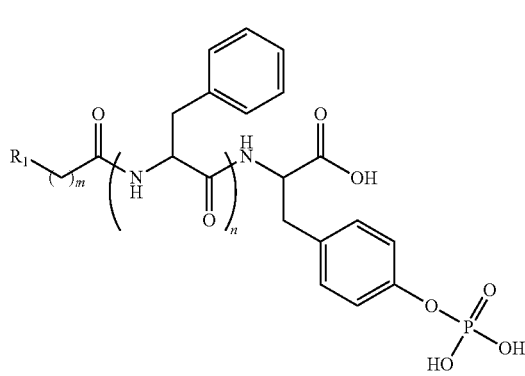

wherein $R_1$ represents a naphthyl group; m represents 1; and n represents 3.

3. A compound represented by formula (II):

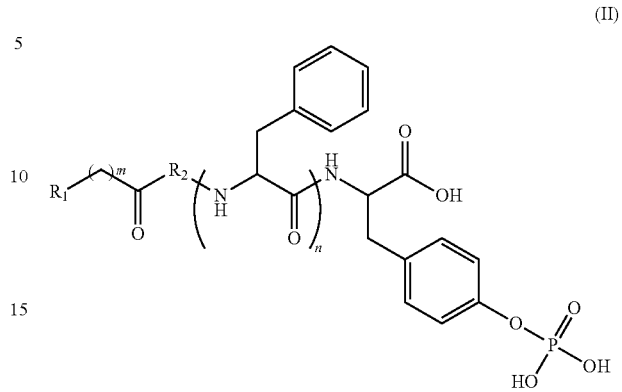

wherein $R_1$ represents a naphthyl, group; $R_2$ represents a glycine residue; m represents 1; and n represents 3.

4. A kit for removing pluripotent cells comprising the compound according to claim 2.

5. A kit for removing pluripotent cells comprising the compound according to claim 3.

* * * * *

UNITED STATES PATENT AND TRADEMARK OFFICE
CERTIFICATE OF CORRECTION

PATENT NO. : 10,689,624 B2
APPLICATION NO. : 15/543488
DATED : June 23, 2020
INVENTOR(S) : Saito et al.

It is certified that error appears in the above-identified patent and that said Letters Patent is hereby corrected as shown below:

In the Specification

Column 3, Line 20: Please correct "n represents an integer of 1 to 6; and represents an integer" to read -- m represents an integer of 1 to 6; and n represents an integer --

Column 6, Line 10, the left section of Formula 5: Please correct "$()_n$" in the portion of Formula 5

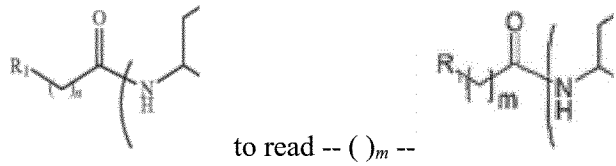

to read -- $()_m$ --

Column 6, Line 20: Please correct "group m" to read -- group; m --

Column 6, Line 44: Please correct "glycine residue; in" to read -- glycine residue; m --

Column 7, Line 41: Please correct "formula" to read -- formula (III): --

Column 15, Line 59: Please correct "1-HS5" to read -- HS5 --

Column 21, Line 9: Please correct "MIHY6-" to read -- MHY6- --

In the Claims

Column 22, Line 38, Claim 1: Please correct "represents, a naphthyl" to read -- represents a naphthyl --

Column 22, Line 64, Claim 1: Please correct "represents, a naphthyl" to read -- represents a naphthyl --

Signed and Sealed this
Tenth Day of November, 2020

Andrei Iancu
*Director of the United States Patent and Trademark Office*

Column 22, Line 65, Claim 1: Please correct "and represents 3" to read -- and n represents 3 --

Column 24, Line 20, Claim 3: Please correct "naphthyl, group" to read -- naphthyl group --